US012600825B2

(12) United States Patent
Wang et al.

(10) Patent No.: US 12,600,825 B2
(45) Date of Patent: Apr. 14, 2026

(54) POLYMER COMPOSITIONS AND BIOSURFACES COMPRISING THEM ON SENSORS

(71) Applicant: Zepto Life Technology, Inc., St. Paul, MN (US)

(72) Inventors: Wei Wang, Saint Paul, MN (US); Frederick William West, Saint Paul, MN (US); Todd Michael Klein, Wayzata, MN (US); Jeremiah James Bolks, Saint Paul, MN (US)

(73) Assignee: Zepto Life Technology, Inc., St. Paul, MN (US)

( * ) Notice: Subject to any disclaimer, the term of this patent is extended or adjusted under 35 U.S.C. 154(b) by 821 days.

(21) Appl. No.: 17/790,461

(22) PCT Filed: Jan. 5, 2021

(86) PCT No.: PCT/US2021/012131
§ 371 (c)(1),
(2) Date: Jun. 30, 2022

(87) PCT Pub. No.: WO2021/141869
PCT Pub. Date: Jul. 15, 2021

(65) Prior Publication Data
US 2023/0039818 A1     Feb. 9, 2023

Related U.S. Application Data

(60) Provisional application No. 62/958,510, filed on Jan. 8, 2020.

(51) Int. Cl.
*C08J 3/24* (2006.01)
*A61L 27/40* (2006.01)
*C08L 71/02* (2006.01)

(52) U.S. Cl.
CPC ............... *C08J 3/246* (2013.01); *A61L 27/40* (2013.01); *C08L 71/02* (2013.01); *C08J 2333/14* (2013.01)

(58) Field of Classification Search
CPC .... C08J 3/246; C08J 2333/14; C08J 2471/02; C08J 3/28; A61L 27/40; C08L 71/02; C08L 33/066; C08L 33/12; C08L 33/14
See application file for complete search history.

(56) References Cited

U.S. PATENT DOCUMENTS 5,371,469 A     12/1994 Anderson
5,646,001 A     7/1997 Terstappen et al.
(Continued)

FOREIGN PATENT DOCUMENTS

CN     101632018 A     1/2010
CN     101855366 A     10/2010
(Continued)

OTHER PUBLICATIONS

Quinn, Photo crosslinked copolymers of 2-hydroxyethyl methacrylate, polyethylene glycol tetra-acrylate and ethylene dimethacrylate for improving biocompatibility of biosensors, Biomaterials 16 1995 389-396 (Year: 1995).*

(Continued)

*Primary Examiner* — Alicia Bland
(74) *Attorney, Agent, or Firm* — Schwegman Lundberg & Woessner, P.A.

(57) ABSTRACT

Polymer compositions comprising, inter alia, at least two hydrophilic polymers and a crosslinking reagent, biosurfaces comprising such polymer compositions, and methods of creating such biosurfaces by disposing such polymer compositions on sensor surfaces are provided. Sensor surfaces coated with such polymer compositions and biosurfaces are amenable, inter alia, to use in methods and devices (Continued)

for detecting, measuring, and/or quantifying one or more analytes in one or more query samples.

20 Claims, 3 Drawing Sheets

(56) References Cited

U.S. PATENT DOCUMENTS

| | | | |
|---|---|---|---|
| 5,683,875 | A | 11/1997 | Lichtenwalter |
| 5,981,297 | A | 11/1999 | Baselt |
| 6,426,043 | B1 | 7/2002 | Cohen et al. |
| 6,437,563 | B1 | 8/2002 | Simmonds et al. |
| 8,889,760 | B2 | 11/2014 | Kurdyumov et al. |
| 9,487,663 | B2 | 11/2016 | Kurdyumov et al. |
| 9,994,721 | B2 | 6/2018 | Kurdyumov et al. |
| 10,253,193 | B2 | 4/2019 | Kurdyumov et al. |
| 10,315,987 | B2 | 6/2019 | Kurdyumov |
| 10,688,493 | B2 | 6/2020 | Kim et al. |
| 2002/0119470 | A1 | 8/2002 | Nerenberg et al. |
| 2003/0027787 | A1* | 2/2003 | Couture ................. A61L 15/60 |
| | | | 536/120 |
| 2003/0044323 | A1 | 3/2003 | Diamond et al. |
| 2003/0153092 | A1 | 8/2003 | Skinner |
| 2005/0085619 | A1 | 4/2005 | Wilson |
| 2006/0115514 | A1 | 6/2006 | Gengrinovitch |
| 2007/0026518 | A1* | 2/2007 | Healy ................. C12N 5/0068 |
| | | | 435/325 |
| 2008/0129286 | A1 | 6/2008 | Kahlman et al. |
| 2008/0190735 | A1 | 8/2008 | Luoma |
| 2008/0246471 | A1 | 10/2008 | Kahlman et al. |
| 2008/0278156 | A1 | 11/2008 | De Boer |
| 2008/0284419 | A1 | 11/2008 | Ikeda |
| 2008/0309329 | A1 | 12/2008 | Kahlman et al. |
| 2009/0066318 | A1 | 3/2009 | Kahlman et al. |
| 2009/0163785 | A1 | 6/2009 | Nelson |
| 2009/0184706 | A1 | 7/2009 | Duric et al. |
| 2010/0259250 | A1 | 10/2010 | Kahlman |
| 2010/0267169 | A1 | 10/2010 | Hajimiri et al. |
| 2010/0323355 | A1 | 12/2010 | Dittmer |
| 2010/0324828 | A1 | 12/2010 | Kahlman et al. |
| 2011/0117676 | A1 | 5/2011 | Ikeda et al. |
| 2011/0241664 | A1 | 10/2011 | Zhang |
| 2012/0003192 | A1* | 1/2012 | Yao ........................ A61L 27/54 |
| | | | 523/113 |
| 2012/0115214 | A1 | 5/2012 | Battrell et al. |
| 2012/0231971 | A1 | 9/2012 | Choi et al. |
| 2012/0315621 | A1 | 12/2012 | Lu et al. |
| 2013/0102489 | A1 | 4/2013 | Osterfeld et al. |
| 2013/0130262 | A1 | 5/2013 | Battrell et al. |
| 2013/0331298 | A1 | 12/2013 | Rea |
| 2013/0343966 | A1 | 12/2013 | Medoro et al. |
| 2014/0120523 | A1 | 5/2014 | Lowery, Jr. et al. |
| 2014/0178900 | A1 | 6/2014 | Jung et al. |
| 2014/0248612 | A1 | 9/2014 | Princen et al. |
| 2014/0292318 | A1 | 10/2014 | Wang et al. |
| 2015/0176065 | A1 | 6/2015 | Powell et al. |
| 2015/0197784 | A1 | 7/2015 | Williams et al. |
| 2015/0198594 | A1 | 7/2015 | Williams et al. |
| 2015/0338427 | A1 | 11/2015 | Pollack et al. |
| 2016/0011182 | A1 | 1/2016 | Qiu |
| 2016/0025756 | A1 | 1/2016 | Pollack et al. |
| 2016/0090633 | A1 | 3/2016 | Platero et al. |
| 2016/0193603 | A1 | 7/2016 | Battrell et al. |
| 2016/0194691 | A1 | 7/2016 | Powell et al. |
| 2016/0209405 | A1 | 7/2016 | Wang et al. |
| 2017/0097337 | A1 | 4/2017 | Shultz et al. |
| 2017/0113221 | A1 | 4/2017 | Hoffman et al. |
| 2017/0241971 | A1 | 8/2017 | Liu et al. |
| 2017/0260567 | A1 | 9/2017 | Selden et al. |
| 2017/0312751 | A1 | 11/2017 | Glezer et al. |
| 2017/0356056 | A1 | 12/2017 | Powell et al. |
| 2018/0021783 | A1 | 1/2018 | Arlett et al. |
| 2018/0067094 | A1 | 3/2018 | Sinha et al. |
| 2018/0099278 | A1 | 4/2018 | Niemeyer et al. |
| 2018/0299407 | A1 | 10/2018 | Haratani et al. |
| 2018/0314046 | A1 | 11/2018 | Sakurai et al. |
| 2019/0283025 | A1 | 9/2019 | Brenk et al. |

FOREIGN PATENT DOCUMENTS

| | | | |
|---|---|---|---|
| CN | 103698320 | A | 4/2014 |
| CN | 104530413 | A | 4/2015 |
| CN | 107513577 | A | 12/2017 |
| CN | 107690581 | A | 2/2018 |
| CN | 109563199 | A | 4/2019 |
| EP | 1936350 | A1 | 6/2008 |
| EP | 3324189 | A1 | 5/2018 |
| JP | 2005180921 | A | 7/2005 |
| JP | 2008511842 | A | 4/2008 |
| JP | 2008522151 | A | 6/2008 |
| JP | 2008544246 | A | 12/2008 |
| JP | 2009008475 | A | 1/2009 |
| JP | 2009511860 | A | 3/2009 |
| JP | 2009511895 | A | 3/2009 |
| JP | 2009530602 | A | 8/2009 |
| JP | 2009236933 | A | 10/2009 |
| JP | 2009249512 | A | 10/2009 |
| JP | 2009250926 | A | 10/2009 |
| JP | 2009539098 | A | 11/2009 |
| JP | 2010500547 | A | 1/2010 |
| JP | 2011503585 | A | 1/2011 |
| JP | 2011221017 | A | 11/2011 |
| JP | 2012516455 | A | 7/2012 |
| JP | 2013518289 | A | 5/2013 |
| JP | 2016509206 | A | 3/2016 |
| JP | 2016534333 | A | 11/2016 |
| JP | 2017082227 | A | 5/2017 |
| JP | 2017520239 | A | 7/2017 |
| JP | 2018507403 | A | 3/2018 |
| JP | 2018525980 | A | 9/2018 |
| KR | 101304323 | B1 | 9/2013 |
| KR | 20160080112 | A | 7/2016 |
| WO | 03054523 | A2 | 7/2003 |
| WO | 2005016115 | A2 | 2/2005 |
| WO | 2006059270 | A2 | 6/2006 |
| WO | 2007042959 | A2 | 4/2007 |
| WO | 2007092909 | A2 | 8/2007 |
| WO | 2008047533 | A1 | 4/2008 |
| WO | 2008101196 | A1 | 8/2008 |
| WO | 2009024922 | A2 | 2/2009 |
| WO | 2009039437 | A1 | 3/2009 |
| WO | 2012085884 | A1 | 6/2012 |
| WO | 2016035197 | A1 | 3/2016 |
| WO | 2016124907 | A1 | 8/2016 |
| WO | 2017030999 | A1 | 2/2017 |
| WO | 2017082227 | A1 | 5/2017 |
| WO | 2018053501 | A1 | 3/2018 |
| WO | 2018057647 | A1 | 3/2018 |
| WO | 2017170238 | A1 | 2/2019 |
| WO | 2021050100 | | 3/2021 |

OTHER PUBLICATIONS

Capanema, Superabsorbent crosslinked carboxymethyl cellulose-PEG hydrogels for potential wound dressing applications, International Journal of Biological Macromolecules 106 2018 1218-1234 (Year: 2018).*

International Search Report and Written Opinion mailed May 27, 2021 in International Patent Application PCT/US2021/012131.

Capanema et al., Superabsorbent crosslinked carboxymethyl cellulose-PEG hydrogels for potential wound dressing applications, International Journal of Biological Macromolecules, vol. 106, Available online Aug. 26, 2017, pp. 1218-1234.

Bajpai, Blood protein adsorption onto macroporous semi-interpenetrating polymer networks (IPNs) of poly(ethylene glycol) (PEG) and poly(2-hydroxyethyl methacrylate) (PH EMA) and assessment of in vitro blood compatibility, Polymer International, vol. 56, Iss. 2, Oct. 31, 2006 [retrieved on Feb. 23, 2021]. Retrieved from the Internet: <URL: https://onlinelibrary.wiley.com/doi/abs/10.1002/pi.2137>. abstract.

(56) References Cited

OTHER PUBLICATIONS

Quinn et al., Photo-crosslinked copolymers of 2-hydroxyethyl methacrylate, poly(ethylene glycol) tetra-acrylate and ethylene dimethacrylate for improving bioc;ompatibility of biosensors, Biomaterials, vol. 16, Iss. 5, 1995 [retrieved on Feb. 23, 2021). Retrieved from the Internet: <URL: https://www.sciencedirect.com/science/article/abs/pii/0142961295988569>. abstract.

Litwin et al., Single molecule FRET methods to study Glutamate receptors, Methods Mol Biol., Author manuscript: available in PMC Jan. 1, 2020, entire document.

"Chinese Application Serial No. 202080077560.0, Office Action mailed Apr. 16, 2025", w/English Translation, 30 pgs.

Giovanni, Rizzi, et al., "Biosensors and Bioelectronics", Denaturation strategies for detection of double stranded PCR products on GMR magnetic biosensor array, (Jul. 15, 2017), 155-160.

Cha et al., "Immobilization of oriented protein molecules on poly-(ethylene glycol)-coated Si(111)", Proteomics, 2004, pp. 1965-1976, vol. 4, WILEY-VCH Verlag Gmbh & Co., Minneapolis, MN.

Zellander et al., "Characterization of Pore Structure in Biologically Functional Poly(2-Hydroxyethyl Methacrylate)—Poly(Ethylene Glycol) Diacrylate (PHEMA-PEGDA)", PLoS One, May 9, 2014, pp. 1-8, vol. 9, Issue 5, Chicago, Illinois.

Doyle et al., "Catalytic Carbene Insertion into C—H Bonds", Chemical Reviews, 2010, pp. 704-724, vol. 110, No. 2, American Chemical Society.

Bayley, "Photogenerated reactive intermediates and their properties", Laboratory Techniques in Biochemistry and Molecular Biology, 1983, Chapter 2, pp. 8-24, vol. 12, Elsevier.

Extended European Search Report issued Aug. 30, 2023 in EP Application No. 20864198.5.

Supplementary Partial European Search Report issued Sep. 14, 2023 in EP Application No. 20913973.2.

Hulme et al., "Incorporation of prefabricated screw, pneumatic, and solenoid valves into microfluidic devices", The Royal Society of Chemistry, Lab Chip, 2009, pp. 79-86, vol. 9, Department of Chemistry and Chemical Biology, Harvard University, Cambridge, MA, USA.

Osterberg et al., "Bead Capture on Magnetic Sensors in a Microfluidic System", IEEE Sensors Journal, Jun. 2009, pp. 682-688, vol. 9, No. 6, Denmark.

Rizzi et al., "Denaturation strategies for detection of double stranded PCR products on GMR magnetic biosensor array", Biosensors and Bioelectronics, 2017, pp. 155-160, Issue 93, Elsevier B.V., Denmark.

Son et al., "Preparation and properties of PEG-modified PHEMA hydro gel and the morphological effect", Macromolecular Research, 2006, pp. 394-399, vol. 14, No. 3, Department of Chemical Engineering, Polymer Technology Institute, Sungkyunkwan University, Suwon, Gyeonggi, Korea.

Sun et al., "Separable detecting of *Escherichia coli* O157H:H7by a giant magneto-resistance-based bio-sensing system", Sensors and Actuators B; Chemical, 2016, pp. 485-492, Elsevier B.V., Shanghai, China.

Teramura et al., "Surface plasmon resonance-based highly sensitive immunosensing for brain natriuretic peptide using nanobeads for signal amplification" Analytical Biochemistry, 2006, pp. 208-215, No. 357, Elsevier Inc., Japan.

"Chinese Application Serial No. 202180017733.4, Office Action mailed Feb. 2, 2024", w English Translation, 20 pgs.

"European Application Serial No. 21738063.3, Extended European Search Report mailed Feb. 14, 2024", 11 pgs.

"International Application Serial No. PCT US2021 012131, International Preliminary Report on Patentability mailed Jul. 21, 2022", 11 pgs.

"Chinese Application Serial No. 202180017733.4, Decision of Rejection mailed May 17, 2024", W Machine English Translation, 35 pgs.

"European Application Serial No. 21738063.3, Response to Communication pursuant to Rules 161(2) and 162 EPC filed Feb. 15, 2023", 6 pgs. 6

Litwin, "Single molecule FRET methods to study Glutamate receptors", Methods Mol Biol., Author manuscript, (Jan. 1, 2020), 1-17.

"European Application Serial No. 21738063.3, Response filed Sep. 3, 2024 to Extended European Search Report mailed Feb. 14, 2024", 12 pgs.

"Chinese Application Serial No. 202180017733.4, Response Filed Aug. 19, 2024 to Decision of Rejection mailed May 17, 2024", w English Claims, 18 pgs.

Bajpai, "Blood protein adsorption onto macroporous semi-interpenetrating polymer networks (IPNs) of poly(ethylene glycol) (PEG) and poly(2-hydroxyethyl methacrylate) (PH EMA) and assessment of in vitro blood compatibility", Polymer International, Oct. 31, 2006, pp. 1-2, vol. 56, Iss. 2, Abstract.

Capanema et al., "Superabsorbent crosslinked carboxymethyl cellulose-PEG hydrogels for potential wound dressing applications" International Journal of Biological Macromolecules, Aug. 26, 2017, pp. 1218-1234, vol. 106, Elsevier Science B.V.

Chu et al., "Bioconjugated Magnetic Nanoparticles for the Detection of Bacteria", Journal of Biomedical Nanotechnology, Dec. 2013, pp. 1951-1961, vol. 9, No. 12, American Scientific Publishers.

Edelstein et al., "The BARC biosensor applied to the detection of biological warfare agents," Biosensors and Bioelectronics, 2000, pp. 805-813, vol. 14, Elsevier Science B.V.

Extended European Search Report dated Mar. 14, 2018 in European Application 15818539.7.

Extended European Search Report issued Apr. 21, 2021 in European Application 19816193.7.

Extended European Search Report issued Mar. 15, 2021 in European Application 19816192.9.

Gaster et al., "Matrix-insensitive protein assays push the limits of biosensors in medicine", Nature Medicine, Technical Reports, Oct. 11, 2009, pp. 1-7.

Graham et al., "Magnetic field-assisted DNA hybridisation and simultaneous detection using micron-sized spin-valve sensors and magnetic nanoparticles", Sensors and Actuators B: Chemical, Feb. 2005, pp. 936-944, vol. 107, Elsevier Science B.V.

Graham et al., "Magnetoresistive-based biosensors and biochips", Trends in Biotechnology, Sep. 2004, pp. 455-462, vol. 22, No. 9, Elsevier Ltd.

Han et al., "A Novel Zero-Drift Detection Method for Highly Sensitive GMR Biochips", IEEE Transactions on Magnetics, IEEE, USA, vol. 42, No. 10, Oct. 1, 2006, pp. 3560-3562.

Han et al., "CMOS Integrated DNA Microarray Based on GMR Sensors", Electron Devices Meeting, 2006. EDM '06. International, IEEE, PI, Dec. 2006, pp. 1-4.

Han et al., "Magnetic Nanotechnology for Biodetection", Journal of the Association for Laboratory Automation, Apr. 2010, pp. 93-98, vol. 15, No. 2, Elsevier.

Huo et al., "A Novel High-Sensitivity Cardiac Multibiomarker Detection System Based on Microfluidic Chip and GMR Sensors", IEEE Transactions on Magnetics, vol. 51, No. 11, Nov. 2015, pp. 1-4.

International Search Report and Written Opinion mailed Jun. 16, 2020 in International Application PCT/US2020/014068.

International Search Report and Written Opinion mailed Nov. 13, 2019 in International Application PCT/US2019/043791.

International Preliminary Report on Patentability issued on Jan. 19, 2017 in International Application PCT/US2015/039747.

International Preliminary Report on Patentability issued Sep. 22, 2020 in International Application PCT/US2019/021837.

International Preliminary Report on Patentability mailed Feb. 11, 2021 in International Application PCT/US2019/043720.

International Preliminary Report on Patentability mailed Feb. 11, 2021 in International Application PCT/US2019/043753.

International preliminary Report on Patentability mailed Feb. 11, 2021 in International Application PCT/US2019/043766.

International Preliminary Report on Patentability mailed Feb. 11, 2021 in International Application PCT/US2019/043791.

International Search Report and Written Opinion mailed May 8, 2019 in International Application PCT/US2019/021837.

International Search Report and Written Opinion mailed Nov. 13, 2019 in International Application PCT/US2019/043720.

(56) References Cited

OTHER PUBLICATIONS

International Search Report and Written Opinion mailed Nov. 13, 2019 in International Application PCT/US2019/043753.
International Search Report and Written Opinion mailed Nov. 15, 2019 in International Application PCT/US2019/043766.
International Search Report and Written Opinion mailed on Dec. 11, 2015 in International Application PCT/US2015/039747.
International Search Report and Written Opinion mailed on Jul. 6, 2020 in International Application PCT/US2020/014570.
Klein et al., "Development of a multiplexed giant magnetoresistive biosensor array prototype to quantify ovarian cancer biomarkers", Biosensors and Bioelectronics, Oct. 23, 2018, pp. 301-307, vol. 126, Elsevier B.V.
Koets et al., "Rapid DNA multi-analyte immunoassay on a magneto-resistance biosensor," Biosensors and Bioelectronics, Oct. 8, 2008, pp. 1893-1898, vol. 24, Elsevier B.V.
Litwin et al., "Single molecule FRET methods to study Glutamate receptors", Methods Mol Biol., Author manuscript; Jan. 1, 2020, pp. 1-17.
Liu et al., "Functional Nucleic Acid Sensors," Chem. Rev., Author Manuscript, May 2009, 109(5), pp. 1948-1998.
Lu et al., "New highly sensitive and selective catalytic DNA biosensors for metal ions", Biosensors and Bioelectronics; 2003; pp. 529-540; vol. 18; Elsevier Science B.V.
Martins et al., "Femtomolar limit of detection with a magnetoresistive biochip," Biosensors and Bioelectronics, Feb. 6, 2008, pp. 2690-2695, vol. 24, Elsevier B.V.
McGhee et al., "DNAzyme sensors for detection of metal ions in the environment and imaging them in living cells", ScienceDirect, Current Opinion in Biotechnology, Apr. 28, 2017, pp. 191-201, vol. 45, Elsevier Ltd.
Quinn et al., "Photo-crosslinked copolymers of 2-hydroxyethyl methacrylate, poly(ethylene glycol) tetra-acrylate and ethylene dimethacrylate for improving biocompatibility of biosensors", Biomaterials, 1995, pp. 1-6, vol. 16, Issue 5, Abstract.

Supplementary European Search Report issued Jan. 5, 2022 in EP Application No. 19816194.5.
Teh et al., "Highly sensitive and selective detection of Pb 2+ ions using a novel and simple DNAzyme-based quartz crystal microbalance with dissipation biosensor", Analyst, Jul. 18, 2014, pp. 5170-5175, vol. 139, The Royal Society of Chemistry.
Tian et al., "Rapid Newcastle Disease Virus Detection Based on Loop-Mediated Isothermal Amplification and Optomagnetic Readout", ACS Sensors, 2016, pp. 1228-1234, vol. 1, ACS Publications.
Wang et al., "Surface Modification for Protein and DNA Immobilization onto GMR Biosensor", IEEE Transactions on Magnetics, Jan. 2013, pp. 296-299, vol. 49, No. 1, IEEE.
Wernette et al., "Incorporation of a DNAzyme into AU-coated nanocapillary array membranes with an internal standard for Pb(II) sensing", The Analyst, , Nov. 24, 2005, pp. 41-47, Issue 131, The Royal Society of Chemistry.
Wu et al., "Comparison of Hydroxylated Print Additives on Antibody Microarray Performance", Journal of Proteome Research, Oct. 19, 2006, pp. 2956-2965, vol. 5, American Chemical Society.
Xu et al., "Giant magnetoresistive biochip for DNA detection and HPV genotyping", Biosensors and Bioelectronics; Apr. 8, 2008; pp. 99-103; vol. 24, Elsevier Science B.V.
Zhu et al., "Functional Nucleic Acid-Based Sensors for Heavy Metal ion Assays," The Analyst, 2014, pp. 6326-6342, vol. 139, No. 4, The Royal Society of Chemistry.
Baselt et al., "A biosensor based on magnetoresistance technology", Biosensors and Bioelectronics, 1998, pp. 731-739, vol. 13, Issues 7-8, Elsevier Science Ltd.
Supplementary European Search Report issued Feb. 7, 2022 in EP Application No. 19840618.3.
Extended European Search Report dated Dec. 5, 2022 in European Application No. 22182712.4.
Yu et al., "Giant Magnetoresistive Biosensors for Molecular Diagnosis: Surface Chemistry and Assay Development", SPIE, vol. 7035, Aug. 2008, pp. 1-9.

* cited by examiner

POLYMER COMPOSITIONS AND BIOSURFACES COMPRISING THEM ON SENSORS

CROSS-REFERENCE TO RELATED APPLICATIONS

The present application is a U.S. National stage entry of International Application PCT/US2021/012131, filed Jan. 5, 2021, which claims priority to U.S. Provisional Patent Application No. 62/958,510, filed Jan. 8, 2020, which is incorporated herein by reference in its entirety.

INTRODUCTION

The present disclosure is generally related to polymer compositions and their use. In particular, the present disclosure relates to the use of polymer compositions to create "biosurfaces" on a sensor. Such biosurfaces comprise polymer compositions and are created, inter alia, by coating sensors with such polymer compositions with the requisite functional handles for biomolecule attachment. Such biosurfaces allow assays to be run at sensor surfaces to detect target analytes in query samples.

Sensors of various type, including Giant Magneto Resistance (GMR) sensors, have enabled development of multiplex assays with high sensitivity and low cost in a compact system. Reliable surface functionalization of sensor structures to anchor biomolecules to perform various assays remains a challenge. The present disclosure provides exemplary solutions.

SUMMARY

In some aspects, embodiments herein relate to polymer compositions comprising: at least two hydrophilic polymers selected from the group consisting of a polyethylene glycol (PEG) polymer, a polysaccharide, and a poly(2-hydroxyethyl methacrylate) (PHEMA) polymer; and a crosslinking reagent crosslinking the at least two hydrophilic polymers. In some embodiments, such polymer compositions do not comprise a block co-polymer of a PEG polymer and a PHEMA polymer.

In some aspects which may be combined with other aspects provided herein, embodiments herein relate to polymer compositions comprising: at least two hydrophilic polymers selected from the group consisting of a polyethylene glycol (PEG) polymer, a cellulose, a starch, a chitin, and alginate, and a dextran, and a poly(2-hydroxyethyl methacrylate) (PHEMA) polymer; and a crosslinking reagent crosslinking the at least two hydrophilic polymers. In some embodiments, such polymer compositions do not comprise a block co-polymer of a PEG polymer and a PHEMA polymer.

In some aspects which may be combined with other aspects provided herein, embodiments herein relate to polymer compositions comprising: a PEG polymer, wherein the PEG polymer has a molecular weight of: about 100 Da to about 50,000 Da; about 100 Da to about 45,000 Da; about 100 Da to about 40,000 Da; about 100 Da to about 35,000 Da, about 100 Da to about 30,000 Da; about 100 Da to about 25,000 Da; about 100 Da to about 20,000 Da; about 100 Da to about 15,000 Da; about 100 Da to about 10,000 Da; about 100 Da to about 8,000 Da, about 100 Da to about 6,000 Da; about 100 Da to about 4,000 Da; about 100 Da to about 2,000 Da; about 100 Da to about 1,000 Da; about 100 Da to about 900 Da; about 100 Da to about 800 Da; about 100 Da to about 700 Da; about 150 Da to about 700 Da; about 200 Da to about 700 Da; or about 200 Da to about 600 Da; a poly(2-hydroxyethyl methacrylate) (PHEMA) polymer; and a crosslinking reagent crosslinking the PEG polymer and the PHEMA polymer. In some embodiments, such polymer compositions do not comprise a block co-polymer of a PEG polymer and a PHEMA polymer.

In some aspects which may be combined with other aspects provided herein, embodiments herein relate to polymer compositions comprising: a polyethylene glycol (PEG) polymer, wherein the PEG polymer is derivatized with one of more functional groups selected from the group consisting of an aldehyde, an alkyne, an amine, an azide, a biotin, a carboxylic acid, a hydroxyl, a maleimide, an epoxy, an N-hydroxysuccinimide (NHS) ester, an orthopyridyl disulfide (OPSS), a sulfonate, a toluenesulfonate (tosyl), a methanesulfonate (mesyl), a 2,2,2-trifluoroethanesulfonate (tresyl), and a thiol; and a crosslinking reagent crosslinking the PEG polymer and the PHEMA polymer. In some embodiments, such polymer compositions do not comprise a block co-polymer of a PEG polymer and a PHEMA polymer.

In some aspects which may be combined with other aspects provided herein, embodiments herein relate to polymer compositions comprising: a polyethylene glycol (PEG) polymer, wherein the PEG polymer is derivatized with one of more functional groups selected from the group consisting of an aldehyde, an alkyne, an amine, an azide, a biotin, a carboxylic acid, a hydroxyl, a maleimide, an epoxy, an N-hydroxysuccinimide (NHS) ester, an orthopyridyl disulfide (OPSS), a sulfonate, a toluenesulfonate (tosyl), a methanesulfonate (mesyl), a 2,2,2-trifluoroethanesulfonate (tresyl), and a thiol; and a crosslinking reagent crosslinking the PEG polymer and the PHEMA polymer, wherein the polyethylene glycol (PEG) polymer is derivatized with one or more N-hydroxysuccinimide (NHS) esters. In some embodiments, such polymer compositions do not comprise a block co-polymer of a PEG polymer and a PHEMA polymer.

In some aspects which may be combined with other aspects provided herein, embodiments herein relate to polymer compositions comprising: a polyethylene glycol (PEG) polymer; a poly(2-hydroxyethyl methacrylate) (PHEMA) polymer, wherein the PHEMA polymer has a molecular weight range of: about 2,000 Daltons (Da) to about 1,000,000 Da; about 4,000 Da to about 950,000 Da; about 6,000 Da to about 900,000 Da; about 8,000 Da to about 850,000 Da, about 10,000 Da to about 800,000 Da; about 12,000 Da to about 750,000 Da; about 14,000 Da to about 700,000 Da; about 16,000 Da to about 650,000 Da; about 16,000 Da to about 600,000 Da; about 16,000 Da to about 550,000 Da, about 16,000 Daltons to about 500,000 Da; about 16,000 Da to about 450,000 Da; about 16,000 Da to about 400,000 Da; about 16,000 Da to about 350,000 Da; about 16,000 Da to about 300,000 Da; about 16,000 Daltons to about 250,000 Da; about 16,000 Da to about 200,000 Da; 16,000 Da to about 150,000 Da; about 16,000 Da to about 100,000 Da, about 16,000 Daltons to about 500,000 Da; about 16,000 Da to about 45,000 Da; about 16,000 Da to about 40,000 Da; about 16,000 Da to about 35,000 Da; about 16,000 Da to about 30,000 Da; about 16,000 Daltons to about 25,000 Da; about 16,000 Da to about 22,000 Da about 18,000 Da to about 22,000 Da; or about 18,000 Daltons to about 20,000 Da; and a crosslinking reagent crosslinking the PEG polymer and the PHEMA polymer. In some embodiments, such polymer compositions do not comprise a block co-polymer of a PEG polymer and a PHEMA polymer.

In some aspects which may be combined with other aspects provided herein, embodiments herein relate to polymer compositions comprising: a polyethylene glycol (PEG) polymer, wherein the PEG polymer is derivatized with one of more functional groups selected from the group consisting of an aldehyde, an alkyne, an amine, an azide, a biotin, a carboxylic acid, a hydroxyl, a maleimide, an epoxy, an N-hydroxysuccinimide (NHS) ester, an orthopyridyl disulfide (OPSS), a sulfonate, a toluenesulfonate (tosyl), a methanesulfonate (mesyl), a 2,2,2-trifluoroethanesulfonate (tresyl), and a thiol, and wherein the derivatized PEG polymer has a molecular weight of: about 100 Daltons (Da) to about 50,000 Da; about 100 Da to about 45,000 Da; about 100 Da to about 40,000 Da; about 100 Da to about 35,000 Da, about 100 Da to about 30,000 Da; about 100 Da to about 25,000 Da; about 100 Da to about 20,000 Da; about 100 Da to about 15,000 Da; about 100 Da to about 10,000 Da; about 100 Da to about 8,000 Da, about 100 Da to about 6,000 Da; about 100 Da to about 4,000 Da; about 100 Da to about 2,000 Da; about 100 Da to about 1,000 Da; about 100 Da to about 900 Da; about 100 Da to about 800 Da; about 100 Da to about 700 Da; about 150 Da to about 700 Da; about 200 Da to about 700 Da; or about 200 Da to about 600 Da; a poly(2-hydroxyethyl methacrylate) (PHEMA) polymer, wherein the PHEMA polymer has a molecular weight range of: about 2,000 Daltons (Da) to about 1,000,000 Da; about 4,000 Da to about 950,000 Da; about 6,000 Da to about 900,000 Da; about 8,000 Da to about 850,000 Da, about 10,000 Da to about 800,000 Da; about 12,000 Da to about 750,000 Da; about 14,000 Da to about 700,000 Da; about 16,000 Da to about 650,000 Da; about 16,000 Da to about 600,000 Da; about 16,000 Da to about 550,000 Da, about 16,000 Daltons to about 500,000 Da; about 16,000 Da to about 450,000 Da; about 16,000 Da to about 400,000 Da; about 16,000 Da to about 350,000 Da; about 16,000 Da to about 300,000 Da; about 16,000 Daltons to about 250,000 Da; about 16,000 Da to about 200,000 Da; 16,000 Da to about 150,000 Da; about 16,000 Da to about 100,000 Da, about 16,000 Daltons to about 500,000 Da; about 16,000 Da to about 45,000 Da; about 16,000 Da to about 40,000 Da; about 16,000 Da to about 35,000 Da; about 16,000 Da to about 30,000 Da; about 16,000 Daltons to about 25,000 Da; about 16,000 Da to about 22,000 Da about 18,000 Da to about 22,000 Da; or about 18,000 Daltons to about 20,000 Da; and a crosslinking reagent crosslinking the PEG polymer and the PHEMA polymer. In some embodiments, such polymer compositions do not comprise a block co-polymer of a PEG polymer and a PHEMA polymer.

In some aspects, which may be combined with other aspects provided herein, embodiments herein relate to polymer compositions comprising: a polyethylene glycol (PEG) polymer, wherein the PEG polymer is derivatized with ab N-hydroxysuccinimide (NHS) ester, and wherein the derivatized PEG polymer has a molecular weight of: about 100 Daltons (Da) to about 50,000 Da; about 100 Da to about 45,000 Da; about 100 Da to about 40,000 Da; about 100 Da to about 35,000 Da, about 100 Da to about 30,000 Da; about 100 Da to about 25,000 Da; about 100 Da to about 20,000 Da; about 100 Da to about 15,000 Da; about 100 Da to about 10,000 Da; about 100 Da to about 8,000 Da, about 100 Da to about 6,000 Da; about 100 Da to about 4,000 Da; about 100 Da to about 2,000 Da; about 100 Da to about 1,000 Da; about 100 Da to about 900 Da; about 100 Da to about 800 Da; about 100 Da to about 700 Da; about 150 Da to about 700 Da; about 200 Da to about 700 Da; or about 200 Da to about 600 Da; a poly(2-hydroxyethyl methacrylate) (PHEMA) polymer, wherein the PHEMA polymer has a molecular weight range of: about 2,000 Daltons (Da) to about 100,000 Da; about 4,000 Da to about 95,000 Da; about 6,000 Da to about 90,000 Da; about 8,000 Da to about 85,000 Da, about 10,000 Da to about 80,000 Da; about 12,000 Da to about 75,000 Da; about 14,000 Da to about 70,000 Da; about 16,000 Da to about 65,000 Da; about 16,000 Da to about 65,000 Da; about 16,000 Da to about 60,000 Da, about 16,000 Daltons to about 55,000 Da; about 16,000 Da to about 50,000 Da; about 16,000 Da to about 45,000 Da; about 16,000 Da to about 40,000 Da; about 16,000 Da to about 35,000 Da; about 16,000 Daltons to about 30,000 Da; about 16,000 Da to about 25,000 Da; about 18,000 Da to about 22,000 Da; or about 18,000 Daltons to about 20,000 Da; and a crosslinking reagent crosslinking the PEG polymer and the PHEMA polymer. In some embodiments, such polymer compositions do not comprise a block co-polymer of a PEG polymer and a PHEMA polymer.

In some aspects, which may be combined with other aspects provided herein, embodiments herein relate to polymer compositions comprising: a polyethylene glycol (PEG) polymer, wherein the PEG polymer is derivatized with an N-hydroxysuccinimide (NHS) ester and wherein the derivatized PEG polymer has a molecular weight of about 600 Da; a poly(2-hydroxyethyl methacrylate) (PHEMA) polymer, wherein the PHEMA polymer has a molecular weight of about 20,000 Da; and a crosslinking reagent crosslinking the PEG polymer and the PHEMA polymer. In some embodiments, such polymer compositions do not comprise a block co-polymer of a PEG polymer and a PHEMA polymer.

In some aspects, which may be combined with other aspects provided herein, embodiments herein relate to polymer compositions comprising at least two hydrophilic polymers and a crosslinking reagent, wherein the crosslinking reagent is represented by Formula (I):

$$\text{PA-L-PA} \tag{I}$$

wherein each PA is independently selected from a photoactivated group or a metal-activated group, and L is a linking group. In some embodiments, each PA independently comprises an azide ($-N_3$), a diazo ($-N_2$) group, an aryl azide, an acyl azide, an azidoformate, a sulfonyl azide, a phosphoryl azide, a diazoalkane, a diazoketone, a diazoacetate, a diazirine, an aliphatic azo, an aryl ketone, benzophenone, acetophenone, anthroquinone, and anthrone. In some embodiments, each PA independently comprises an azide ($-N_3$), or a diazo ($-N_2$) group. In some embodiments, such polymer compositions do not comprise a block co-polymer of a PEG polymer and a PHEMA polymer.

In some aspects, which may be combined with other aspects provided herein, embodiments herein relate to polymer compositions comprising at least two hydrophilic polymers and a crosslinking reagent, wherein the crosslinking reagent is represented by Formula (I):

$$\text{PA-L-PA} \tag{I}$$

wherein each PA is independently selected from a photoactivated group or a metal-activated group, and L is a linking group, wherein: each PA independently comprises an azide ($-N_3$), a diazo ($-N_2$) group, an aryl azide, an acyl azide, an azidoformate, a sulfonyl azide, a phosphoryl azide, a diazoalkane, a diazoketone, a diazoacetate, a diazirine, an aliphatic azo, an aryl ketone, benzophenone, acetophenone, anthroquinone, and anthrone; L comprises at least one Y and one or more X, wherein: (a) each at least one Y is independently selected from the group consisting of: an optionally substituted divalent alkylene; an optionally substituted arylene; and optionally substituted divalent heteroaromatic ring moiety; having from 1 to 20 atoms; an alkylene, $-(CR_2)_p-$, wherein p is an integer from 1 to 10, 1 to 6, or 1 to 4, and wherein $R_2$ is independently selected from the group consisting of H and lower alkyl, $C_1$-$C_5$ alkyl, and $C_1$-$C_3$ alkyl; and/or a divalent heteroaromatic ring having from 4 to 20 carbon atoms and contains at least one heteroatom selected from the group consisting of O, N, and S; and (b) each X is independently selected from the group consisting of alkylene, —$NR_1$—, —O—, —S—, —S—S—, —CO—$NR_1$—, —CO—O—, —O—CO—, —CO—, and a bond, wherein $R_1$ is independently selected from the group consisting of H and lower alkyl. In some embodiments, such polymer compositions do not comprise a block co-polymer of a PEG polymer and a PHEMA polymer.

In some aspects, which may be combined with other aspects provided herein, embodiments herein relate to polymer compositions comprising at least two hydrophilic polymers and a crosslinking reagent, wherein the crosslinking reagent is represented by Formula (II):

$$PA\text{-}Y_1\text{-}X_1\text{-}X_2\text{-}X_3\text{-}X_4\text{-}X_5\text{-}X_6\text{-}X_7\text{-}X_8\text{-}X_9\text{-}Y_2\text{-}PA \qquad (II)$$

wherein each PA is a photo-activated group or a metal-activated group, and $Y_1$-$X_1$-$X_2$-$X_3$-$X_4$-$X_5$-$X_6$-$X_7$-$X_8$-$X_9$-$Y_2$ is a linking group. In some embodiments, each PA independently comprises an azide (—$N_3$), a diazo (—$N_2$) group, an aryl azide, an acyl azide, an azidoformate, a sulfonyl azide, a phosphoryl azide, a diazoalkane, a diazoketone, a diazoacetate, a diazirine, an aliphatic azo, an aryl ketone, benzophenone, acetophenone, anthroquinone, and anthrone. In some embodiments, each PA independently comprises an azide (—$N_3$), or a diazo (—$N_2$) group. In some embodiments, such polymer compositions do not comprise a block co-polymer of a PEG polymer and a PHEMA polymer.

In some aspects, which may be combined with other aspects provided herein, embodiments herein relate to polymer compositions comprising at least two hydrophilic polymers and a crosslinking reagent, wherein the crosslinking reagent is represented by Formula (II):

$$PA\text{-}Y_1\text{-}X_1\text{-}X_2\text{-}X_3\text{-}X_4\text{-}X_5\text{-}X_6\text{-}X_7\text{-}X_8\text{-}X_9\text{-}Y_2\text{-}PA \qquad (II)$$

wherein each PA is a photo-activated group or a metal-activated group, and $Y_1$-$X_1$-$X_2$-$X_3$-$X_4$-$X_5$-$X_6$-$X_7$-$X_8$-$X_9$-$Y_2$ is a linking group, wherein: each PA independently comprises an azide (—$N_3$), a diazo (—N2) group, an aryl azide, an acyl azide, an azidoformate, a sulfonyl azide, a phosphoryl azide, a diazoalkane, a diazoketone, a diazoacetate, a diazirine, an aliphatic azo, an aryl ketone, benzophenone, acetophenone, anthroquinone, and anthrone; each of $Y_1$, and $Y_2$ is independently selected from the group consisting of: an optionally substituted divalent alkylene; an optionally substituted arylene; and optionally substituted divalent heteroaromatic ring moiety; having from 1 to 20 atoms; an alkylene, —$(CR_2)_p$—, wherein p is an integer from 1 to 10, 1 to 6, or 1 to 4, and wherein $R_2$ is independently selected from the group consisting of H and lower alkyl, $C_1$-$C_5$ alkyl, and $C_1$-$C_3$ alkyl; and/or a divalent heteroaromatic ring having from 4 to 20 carbon atoms and contains at least one heteroatom selected from the group consisting of O, N, and S; and each of $X_1$, $X_2$, $X_3$, $X_4$, $X_5$, $X_6$, $X_7$, $X_8$, and $X_9$ is independently selected from the group consisting of alkylene, —$NR_1$—, —O—, —S—, —S—S—, —CO—$NR_1$—CO—, —CO—O—, —O—CO—, —CO—, and a bond, wherein $R_1$ is independently selected from the group consisting of H and lower alkyl. In some embodiments, such polymer compositions do not comprise a block co-polymer of a PEG polymer and a PHEMA polymer.

In some embodiments, the crosslinking reagent comprises bis[2-(4-azidosalicylamido)ethyl]disulfide or dithiobis(phenylazide).

In some aspects, which may be combined with other aspects provided herein, embodiments herein relate to polymer compositions wherein at least one of the at least two hydrophilic polymers comprises a branched polyethylene glycol (PEG) polymer. In some embodiments, such polymer compositions do not comprise a block co-polymer of a PEG polymer and a PHEMA polymer.

In some aspects, which may be combined with other aspects provided herein, embodiments herein relate to polymer compositions wherein at least one of the at least two hydrophilic polymers comprises 4-arm PEG, 8-arm PEG, 4-arm PEG-OH, 8-arm PEG-OH, 4-arm PEG-acrylate, 8-arm PEG-acrylate, 4-arm PEG-acrylamide, 8-arm PEG-acrylamide, 4-arm PEG-amine, 8-arm PEG-amine, 4-arm PEG-thiol, 8-arm PEG thiol, 4-arm PEG maleimide, 8-arm PEG maleimide, 4-arm PEG-succinimidyl carboxymethyl ester (NHS), 8-arm PEG-succinimidyl carboxymethyl ester (NHS), 4-arm PEG-succinimidyl glutarate ester, 8-arm PEG-succinimidyl glutarate ester, 4-arm PEG-succinimidyl succinate ester, 8-arm PEG-succinimidyl succinate ester, 4-arm PEG-glutaramide succinimidyl ester, 8-arm PEG-glutaramide succinimidyl ester, 4-arm PEG-succinimide succinimidyl ester, 8-arm PEG-succinimide succinimidyl ester, 4-arm PEG-epoxide, 8-arm PEG-epoxide, 4-arm PEG 4-nitrophenyl carbonate (NPC), 8-arm PEG 4-nitrophenyl carbonate (NPC), 4-arm PEG-acetic acid, 8-arm PEG-acetic acid, 4-arm PEG-glutaric acid, 8-arm PEG-glutaric acid, 4-arm PEG-succinic acid, 8-arm PEG-succinic acid, 4-arm PEG-glutaramide acid, 8-arm PEG-glutaramide acid, 4-arm PEG-succinimide acid, 8-arm PEG-succinimide acid, 4-arm PEG-azide, 8-arm PEG-azide, 4-arm PEG-alkyne, or 8-arm PEG-alkyne. In some embodiments, such polymer compositions do not comprise a block co-polymer of a PEG polymer and a PHEMA polymer.

In some aspects, which may be combined with other aspects provided herein, embodiments herein relate to polymer compositions further comprising a covalently attached biomolecule. In some embodiments, such polymer compositions do not comprise a block co-polymer of a PEG polymer and a PHEMA polymer.

In some aspects, which may be combined with other aspects provided herein, embodiments herein relate to polymer compositions further comprising a covalently attached biomolecule comprising a protein, a transcription factor, a nucleic acid, a deoxyribonucleic acid, a ribonucleic acid, a polynucleotide, a double-stranded DNA (dsDNA), a single stranded DNA (ssDNA), a hybrid double-stranded polynucleotide comprising a ssDNA and a ssRNA, an oligonucleotide, a carbohydrate, a hormone, a glycoprotein, an immunoglobulins, an antibody, or antigen-binding antibody fragment. In some embodiments, the covalently attached biomolecule comprises a double-stranded DNA (dsDNA). In some embodiments, the covalently attached biomolecule comprises a protein. In some embodiments, the covalently attached biomolecule comprises an antibody, an immunoglobulin, or an antigen-binding antibody fragment. In some embodiments, such polymer compositions do not comprise a block co-polymer of a PEG polymer and a PHEMA polymer.

In some aspects, which may be combined with other aspects provided herein, embodiments herein relate to biosurfaces comprising a polymer composition comprising at least two hydrophilic polymers and a crosslinking reagent disposed as a layer on a sensor, wherein the biosurfaces are prepared by a method comprising crosslinking the at least two hydrophilic polymers with the crosslinking reagent. In some embodiments, such polymer compositions do not comprise a block co-polymer of a PEG polymer and a PHEMA polymer.

In some aspects, which may be combined with other aspects provided herein, embodiments herein relate to bio- surfaces comprising a polyethylene glycol (PEG) polymer; a poly(2-hydroxyethyl methacrylate) (PHEMA) polymer; and a crosslinking reagent crosslinking PEG and PHEMA, wherein the biosurfaces are prepared by a method compris- ing crosslinking the at least two hydrophilic polymers with the crosslinking reagent. In some embodiments, such bio- surfaces do not comprise a block co-polymer of a PEG polymer and a PHEMA polymer.

In some aspects, which may be combined with other aspects provided herein, embodiments herein relate to bio- surfaces prepared by crosslinking a polyethylene glycol (PEG) polymer and a poly(2-hydroxyethyl methacrylate) (PHEMA) polymer with a crosslinking reagent represented by either Formula (I): PA-L-PA or Formula (II) PA-$Y_1$-$X_1$-$X_2$-$X_3$-$X_4$-$X_5$-$X_6$-$X_7$-$X_8$-$X_9$-$Y_2$-PA wherein each PA is a photo- or metal-activated or activated group, and L is a linking group. In some embodiments, such biosurfaces do not comprise a block co-polymer of a PEG polymer and a PHEMA polymer.

In some aspects, which may be combined with other aspects provided herein, embodiments herein relate to meth- ods of making a polymer composition comprising crosslink- ing a PEG polymer and a PHEMA polymer with a cross- linking reagent. In some embodiments, polymer compositions made by such methods do not comprise a block co-polymer of a PEG polymer and a PHEMA polymer.

In some aspects, which may be combined with other aspects provided herein, embodiments herein relate to meth- ods of making a biosurface comprising crosslinking a PEG polymer and the PHEMA polymer with a crosslinking reagent. In some embodiments, biosurfaces made by such methods do not comprise a block co-polymer of a PEG polymer and a PHEMA polymer.

In some aspects, which may be combined with other aspects provided herein, embodiments herein relate to meth- ods of making a biosurface comprising coating a sensor with a polymer composition comprising at least two hydrophilic polymers and a crosslinking reagent and crosslinking the at least two hydrophilic polymers with the crosslinking reagent. In some embodiments, biosurfaces made by such methods do not comprise a block co-polymer of a PEG polymer and a PHEMA polymer.

In some aspects, which may be combined with other aspects provided herein, embodiments herein relate to meth- ods of making a polymer composition comprising crosslink- ing a PEG polymer and a PHEMA polymer with a cross- linking reagent. In some embodiments, polymer compositions made by such methods do not comprise a block co-polymer of a PEG polymer and a PHEMA polymer.

In some aspects, which may be combined with other aspects provided herein, embodiments herein relate to meth- ods of making a polymer composition comprising coating a sensor with a polymer composition comprising at least two hydrophilic polymers and a crosslinking reagent and cross- linking the at least two hydrophilic polymers with the crosslinking reagent. In some embodiments, polymer com- positions made by such methods do not comprise a block co-polymer of a PEG polymer and a PHEMA polymer.

In some embodiments, the crosslinking comprises photo- catalysis.

In some embodiments, the crosslinking comprises metal catalysis.

In some aspects, which may be combined with other aspects provided herein, embodiments relate to polymer composition comprising: a polyethylene glycol (PEG) poly- mer; a poly(2-hydroxyethyl methacrylate) (PHEMA) poly- mer; and a crosslinking reagent represented by Formula (I):

$$PA\text{-}L\text{-}PA \tag{I}$$

wherein: each PA independently comprises an azide (—$N_3$), a diazo (—$N_2$) group, an aryl azide, an acyl azide, an azidoformate, a sulfonyl azide, a phosphoryl azide, a diazo- alkane, a diazoketone, a diazoacetate, a diazirine, an ali- phatic azo, an aryl ketone, benzophenone, acetophenone, anthroquinone, and anthrone; L comprises at least one Y and one or more X, wherein: each at least one Y is independently selected from the group consisting of: an optionally substi- tuted divalent alkylene; an optionally substituted arylene; and optionally substituted divalent heteroaromatic ring moi- ety; having from 1 to 20 atoms; an alkylene, —$(CR_2)_p$—, wherein p is an integer from 1 to 10, 1 to 6, or 1 to 4, and wherein $R_2$ is independently selected from the group con- sisting of H and lower alkyl, $C_1$-$C_5$ alkyl, and $C_1$-$C_3$ alkyl; and/or a divalent heteroaromatic ring having from 4 to 20 carbon atoms and contains at least one heteroatom selected from the group consisting of O, N, and S; and each X is independently selected from the group consisting of alkylene, —$NR_1$—, —O—, —S—, —S—S—, —CO— $NR_1$—, —$NR_1$—CO—, —CO—O—, —O—CO—, —CO—, and a bond, wherein $R_1$ is independently selected from the group consisting of H and lower alkyl. In some embodiments, such polymer compositions do not comprise a block co-polymer of a PEG polymer and a PHEMA polymer.

In some aspects, which may be combined with other aspects provided herein, embodiments relate to polymer composition comprising: a polyethylene glycol (PEG) poly- mer; a poly(2-hydroxyethyl methacrylate) (PHEMA) poly- mer; and a crosslinking reagent represented by Formula (II):

$$PA\text{-}Y_1\text{-}X_1\text{-}X_2\text{-}X_3\text{-}X_4\text{-}X_5\text{-}X_6\text{-}X_7\text{-}X_8\text{-}X_9\text{-}Y_2\text{-}PA \tag{II}$$

wherein each PA is a photo-activated group or a metal- activated group, and $Y_1$-$X_1$-$X_2$-$X_3$-$X_4$-$X_5$-$X_6$-$X_7$-$X_8$-$X_9$-$Y_2$ is a linking group, wherein: each PA independently com- prises an azide (—$N_3$), a diazo (—$N_2$) group, an aryl azide, an acyl azide, an azidoformate, a sulfonyl azide, a phospho- ryl azide, a diazoalkane, a diazoketone, a diazoacetate, a diazirine, an aliphatic azo, an aryl ketone, benzophenone, acetophenone, anthroquinone, and anthrone; each of Y, $Y_1$, and $Y_2$ is independently selected from the group consisting of: an optionally substituted divalent alkylene; an optionally substituted arylene; and optionally substituted divalent het- eroaromatic ring moiety; having from 1 to 20 atoms; an alkylene, —$(CR_2)_p$—, wherein p is an integer from 1 to 10, 1 to 6, or 1 to 4, and wherein $R_2$ is independently selected from the group consisting of H and lower alkyl, $C_1$-$C_5$ alkyl, and $C_1$-$C_3$ alkyl; and/or a divalent heteroaromatic ring having from 4 to 20 carbon atoms and contains at least one heteroatom selected from the group consisting of O, N, and S; and each of $X_1$, $X_2$, $X_3$, $X_4$, $X_5$, $X_6$, $X_7$, $X_8$, and $X_9$ is independently selected from the group consisting of alkylene, —$NR_1$—, —O—, —S—, —S—S—, —CO— $NR_1$—, —$NR_1$—CO—, —CO—O—, —O—CO—, —CO—, and a bond, wherein $R_1$ is independently selected from the group consisting of H and lower alkyl. In some embodiments, the PEG polymer is derivatized with an N-hydroxysuccinimide (NHS) ester and wherein the deriva- tized PEG polymer has a molecular weight of about 600 Da.

In some embodiments, such polymer compositions do not comprise a block co-polymer of a PEG polymer and a PHEMA polymer.

In some aspects, which may be combined with other aspects provided herein, embodiments relate to polymer compositions comprising: a least two hydrophilic polymers selected from the group consisting of a polyethylene glycol (PEG) polymer, a polysaccharide, and a poly(2-hydroxy-ethyl methacrylate) (PHEMA) polymer; and a crosslinking reagent crosslinking the at least two hydrophilic polymers. In some embodiments, such polymer compositions do not comprise a block co-polymer of a PEG polymer and a PHEMA polymer Other aspects, features, and advantages of the present disclosure will become apparent from the following detailed description, the accompanying drawings, and the appended claims.

BRIEF DESCRIPTION OF THE DRAWINGS

FIG. 2A depicts the fluorescence units observed upon analysis of biosurfaces prepared as described in Example 1 and assayed as described in Example 2 using 0.05 mg/mL, 0.1 mg/mL, 0.2 mg/mL, 0.3 mg/mL, or 0.5 mg/mL of dithiobis(phenylazide) as the crosslinking reagent. FIG. 2B provides an fluorescence microarray image of a biosurface.

DETAILED DESCRIPTION

Figure 1:
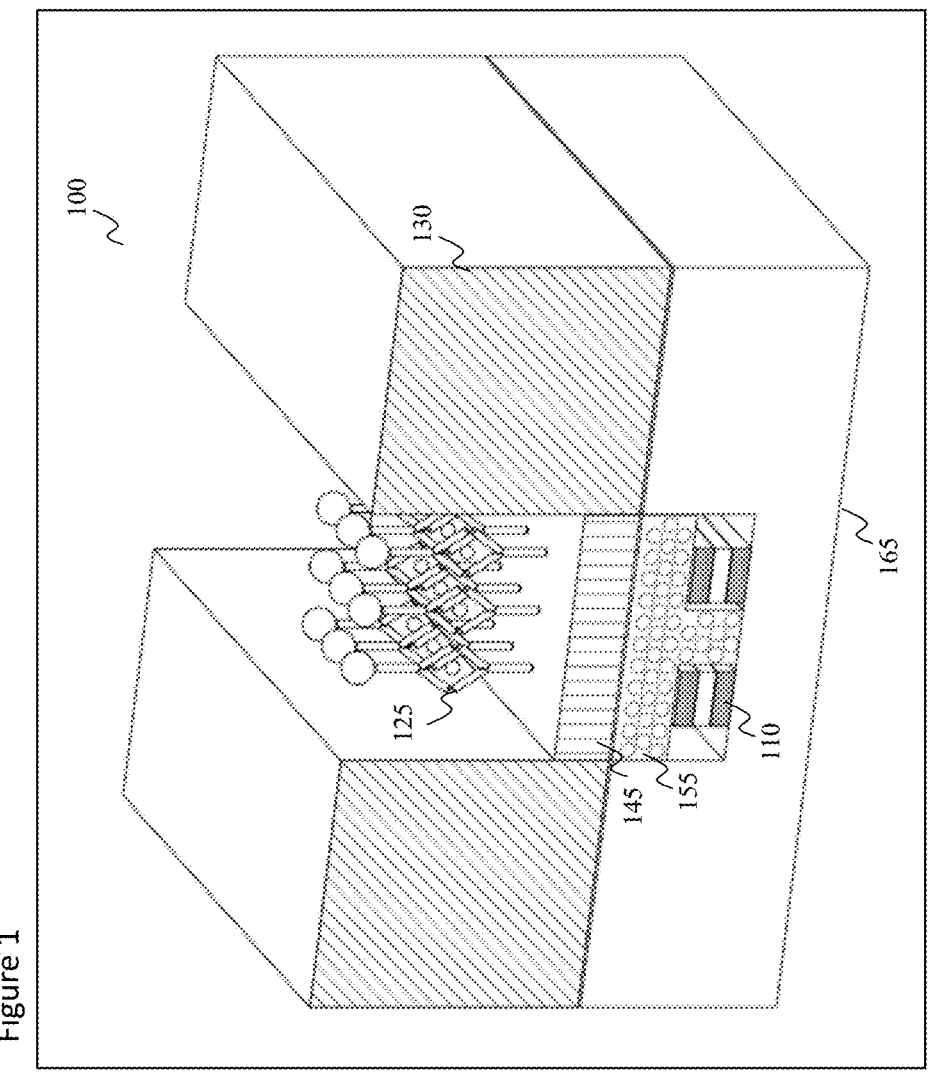
FIG. 1 shows a cross-section representation of a micro-fluidic channel with a sensor residing therein along with a biosurface layer disposed over the sensor, in accordance with an embodiment.

This disclosure relates, inter alia, to polymer compositions that may be employed of functionalize sensor surfaces, such as, for example, Giant Magneto-Resistive (GMR) sensors, and methods of functionalizing the surfaces of such sensors. Such polymer compositions may be attached to sensor surfaces and may further comprise one or more biomolecules. Such polymer compositions that further comprise one or more biomolecules are also examples of poly-mer compositions. Sensors, such as, for example, GMR sensors, that are functionalized as disclosed herein and throughout may be used to detect one or more analytes in on or more query samples using devises and/or methods that comprise such sensors and/or their use.

In some embodiments, such polymer compositions are provided, which may be crosslinked. In some embodiments, polymer compositions are provided, which may be cross-linked and attached to a sensor surface, such as a GMR sensor surface. In some embodiments, a polymer composi-tion is crosslinked so that it is attached to a sensor surface, and a biomolecule is subsequently attached to the polymer composition that has been attached to the sensor surface. In some embodiments, a polymer composition is crosslinked and a biomolecule is attached to the crosslinked composi-tion, and then the crosslinked composition and attached biomolecule is attached to a sensor surface.

In some embodiments, provided are biosurfaces compris-ing polymer compositions. In some embodiments, a biosur-face comprises a crosslinked polymer composition. In some embodiments a biosurface further comprises one or more biomolecules. In some embodiments a biosurface may further comprise one or more biomolecules that is/are attached to a polymer composition. In some embodiments, a biosur-face comprises a crosslinked polymer composition compris-ing a biomolecule. In some embodiments, a biosurface comprises a crosslinked polymer composition, and further comprises a biomolecule. In some embodiments, a biomo-lecule is covalently attached to the polymer composition, which is attached to a sensor surface.

The term "biosurface" refers a polymer composition as disclosed herein that is disposed on a sensor surface, such as a GMR surface. Such "biosurfaces" may be used to generate sensor surfaces that may be employed to detect, measure, and/or quantify one or more analytes in one or more query samples. A biosurface may be created by disposing a poly-mer composition disclosed herein on a sensor surface (also referred to as a "substrate", which may be used interchange-ably throughout). A biosurface may may further comprise a biomolecule attached to a polymer composition, which is disposed on a sensor surface, such as a GMR sensor. Accordingly, in some embodiments, a "biosurface" com-prises a polymer composition and biomolecule that is attached to the polymer composition simultaneous with, or subsequent to, disposing the polymer composition on the surface of the substrate.

As used herein, "biomolecule" refers to any molecule having some role in a biological context and include, with-out limitation, proteins, transcription factors, nucleic acids, deoxyribonucleic acids, ribonucleic acids, polynucleotides, double-stranded DNS (dsDNA), single stranded DNA (ssDNA), a hybrid double-stranded polynucleotide compris-ing a ssDNA and a ssRNA, oligonucleotides, carbohydrates, hormones, glycoproteins, immunoglobulins, antibodies, antigen-binding antibody fragments, and the like.

Referring now to FIG. 1 as an exemplary, non-limiting embodiment, there is shown a cross-sectional view of a microfluidic channel 100 having a channel body 130 and an exemplary GMR sensor 110 disposed at the bottom 165 of channel 100. Biomolecule 125 is immobilized with respect to the sensor via attachment as a component of a biosurface 145. In this exemplary, non-limiting embodiment, biosur-face 145 comprises a crosslinked polymer composition. Between biosurface 145 and GMR sensor 110 is an optional insulating layer 155. Insulating layer 155 may be, for example, a metal oxide layer. Without being bound by theory, embodiments disclosed herein provide polymer com-positions that serve as effective materials for creating bio-surface 145, which biosurface 145 may further comprise biomolecule 125, where conventional surface materials have underperformed.

In some embodiments, a polymer composition comprises at least two hydrophilic polymers and a crosslinking reagent. In some embodiments, at least one of the at least two hydrophilic polymers contain polar or charged functional groups, rendering them soluble in aqueous solution, such as in water. Numerous hydrophilic polymers that are available to the skilled artisan may be employed to generate polymer compositions and biosurfaces, such as, for example: acryl-ics, including acrylic acids, acrylamides, poly(2-hydroxy-ethyl methacrylate) (PHEMA), and maleic anhydride poly-mers and copolymers; amine-functional polymers include allylamine, ethyleneimine, oxazoline, and other polymers containing amine groups in their main- or side-chains; starches; chitins; alginates; dextrans; and celluloses.

In some embodiments, a polymer composition comprises at least two hydrophilic polymers selected from the group consisting of a polyethylene glycol (PEG) polymer, a poly-saccharide, and a poly(2-hydroxyethyl methacrylate)

(PHEMA) polymer; and a crosslinking reagent crosslinking the at least two hydrophilic polymers. In some embodiments, such polymer compositions do not comprise a block co-polymer of a PEG polymer and a PHEMA polymer In some embodiments, a polymer composition comprises at least two hydrophilic polymers selected from the group consisting of a polyethylene glycol (PEG) polymer, a cellulose, a starch, a chitin, and alginate, and a dextran, and a poly(2-hydroxyethyl methacrylate) (PHEMA) polymer; and a crosslinking reagent crosslinking the at least two hydrophilic polymers. In some embodiments, such polymer compositions do not comprise a block co-polymer of a PEG polymer and a PHEMA polymer.

In some embodiments, at least one of the at least two hydrophilic polymers comprises a polyethylene glycol (PEG) polymer. In some embodiments, at least one of the at least two hydrophilic polymers comprises a derivatized polyethylene glycol (PEG) polymer. In some embodiments, at least one of the at least two hydrophilic polymers comprises a polyethylene glycol (PEG) polymer that is derivatized with one of more functional groups selected from the group consisting of an aldehyde, an alkyne, an amine, an azide, a biotin, a carboxylic acid, a hydroxyl, a maleimide, an epoxy, an N-hydroxysuccinimide (NHS) ester, an orthopyridyl disulfide (OPSS), a sulfonate, a toluene-sulfonate (tosyl), a methanesulfonate (mesyl), a 2,2,2-trifluoroethanesulfonate (tresyl), and a thiol. In some embodiments, at least one of the at least two hydrophilic polymers comprises a polyethylene glycol (PEG) polymer that is derivatized with one or more N-hydroxysuccinimide (NHS) esters. In is to be understood that, as used herein and throughout, a "derivatized polyethylene glycol (PEG) polymer" is, itself, a "polyethylene glycol (PEG) polymer" or a "PEG polymer", used interchangeably throughout.

In some embodiments, the PEG polymer may be branched, such as multi-arm PEG polymers. Exemplary compounds of this type include, without limitation, 4-arm PEG, 8-arm PEG, 4-arm PEG-OH, 8-arm PEG-OH, 4-arm PEG-acrylate, 8-arm PEG-acrylate, 4-arm PEG-acrylamide, 8-arm PEG-acrylamide, 4-arm PEG-amine, 8-arm PEG-amine, 4-arm PEG-thiol, 8-arm PEG thiol, 4-arm PEG maleimide, 8-arm PEG maleimide, 4-arm PEG-succinimidyl carboxymethyl ester (NHS), 8-arm PEG-succinimidyl carboxymethyl ester (NHS), 4-arm PEG-succinimidyl glutarate ester, 8-arm PEG-succinimidyl glutarate ester, 4-arm PEG-succinimidyl succinate ester, 8-arm PEG-succinimidyl succinate ester, 4-arm PEG-glutaramide succinimidyl ester, 8-arm PEG-glutaramide succinimidyl ester, 4-arm PEG-succinimide succinimidyl ester, 8-arm PEG-succinimide succinimidyl ester, 4-arm PEG-epoxide, 8-arm PEG-epoxide, 4-arm PEG 4-nitrophenyl carbonate (NPC), 8-arm PEG 4-nitrophenyl carbonate (NPC), 4-arm PEG-acetic acid, 8-arm PEG-acetic acid, 4-arm PEG-glutaric acid, 8-arm PEG-glutaric acid, 4-arm PEG-succinic acid, 8-arm PEG-succinic acid, 4-arm PEG-glutaramide acid, 8-arm PEG-glutaramide acid, 4-arm PEG-succinimide acid, 8-arm PEG-succinimide acid, 4-arm PEG-azide, 8-arm PEG-azide, 4-arm PEG-alkyne, or 8-arm PEG-alkyne, which are commercially available from, for example, Creative PEGWorks (Chapel Hill, NC).

In some embodiments, the terminal PEG moieties may comprise a leaving group, such as halo, mesylate, tosylate, amine, carboxyl, epoxy, aziridine, thiol, and the like. The terminal PEG group or groups may be converted to a variety of functional group handles including, without limitation, amine, carboxyl, thiol, epoxy, hydroxy, alkyne, azide, alkyne, and the like. These functional group handles may serve as covalent bonding attachment points, for example, for securing biomolecules to the biosurface. In some such embodiments, the terminal group may be a precursor for cycloaddition chemistry, such as [4+2], [4+1] or [3+2] cycloadditions, and the like. Such reactions include, azide-alkyne cycloaddition (Huisgen 1,3 dipolar cycloaddition), Diels-Alder reaction (diene and alkene, both normal mode and inverse electron demand), thiol-ene reaction, and the like. Accordingly, the PEG can terminate in a functional handle that enable so-called click chemistry. Exemplary functional groups facilitate click chemistry include, without limitation, azides, alkynes, thiol, alkenes, isonitrile, and tetrazine.

In some embodiments, at least one of the at least two hydrophilic polymers comprises a PEG polymer, wherein the PEG polymer has a number average molecular weight of: about 100 Da to about 50,000 Da; about 100 Da to about 45,000 Da; about 100 Da to about 40,000 Da; about 100 Da to about 35,000 Da, about 100 Da to about 30,000 Da; about 100 Da to about 25,000 Da; about 100 Da to about 20,000 Da; about 100 Da to about 15,000 Da; about 100 Da to about 10,000 Da; about 100 Da to about 8,000 Da, about 100 Da to about 6,000 Da; about 100 Da to about 4,000 Da; about 100 Da to about 2,000 Da; about 100 Da to about 1,000 Da; about 100 Da to about 900 Da; about 100 Da to about 800 Da; about 100 Da to about 700 Da; about 150 Da to about 700 Da; about 200 Da to about 700 Da; or about 200 Da to about 600 Da.

In some embodiments, PEG polymers may terminate in other organic functional groups including, hydroxyl groups (—OH). Any terminal functional group on the PEG polymer may be converted into other functional groups before or after crosslinking. In some embodiments, the terminal groups of the PEG polymer portion of the polymer compositions disclosed herein may serve as the attachment point for various biomolecules to provide a biosurface. Thus, for example, the NHS of an NHS-PEG-NHS group may be utilized for attachment of a biomolecule. Referring back to FIG. 1 as an exemplary, non-limiting example, biosurface 145 may also be linked to insulating layer 155 through terminal PEG chemical moieties as well. In some embodiments, at least one of the at least two hydrophilic polymers comprises a poly(2-hydroxyethyl methacrylate) (PHEMA) polymer.

In some embodiments, the PHEMA polymer has a number average molecular weight range of: about 2,000 Daltons (Da) to about 100,000 Da; about 4,000 Da to about 95,000 Da; about 6,000 Da to about 90,000 Da; about 8,000 Da to about 85,000 Da, about 10,000 Da to about 80,000 Da; about 12,000 Da to about 75,000 Da; about 14,000 Da to about 70,000 Da; about 16,000 Da to about 65,000 Da; about 16,000 Da to about 65,000 Da; about 16,000 Da to about 60,000 Da, about 16,000 Daltons to about 55,000 Da; about 16,000 Da to about 50,000 Da; about 16,000 Da to about 45,000 Da; about 16,000 Da to about 40,000 Da; about 16,000 Da to about 35,000 Da; about 16,000 Daltons to about 30,000 Da; about 16,000 Da to about 25,000 Da; about 18,000 Da to about 22,000 Da; or about 18,000 Daltons to about 20,000 Da.

In some embodiments, a polymer composition comprises a PEG polymer, wherein the PEG polymer has a number average molecular weight of: about 100 Da to about 50,000 Da; about 100 Da to about 45,000 Da; about 100 Da to about 40,000 Da; about 100 Da to about 35,000 Da, about 100 Da to about 30,000 Da; about 100 Da to about 25,000 Da; about 100 Da to about 20,000 Da; about 100 Da to about 15,000 Da; about 100 Da to about 10,000 Da; about 100 Da to about 8,000 Da, about 100 Da to about 6,000 Da; about 100 Da to about 4,000 Da; about 100 Da to about 2,000 Da; about 100 Da to about 1,000 Da; about 100 Da to about 900 Da; about 100 Da to about 800 Da; about 100 Da to about 700 Da; about 150 Da to about 700 Da; about 200 Da to about 700 Da; or about 200 Da to about 600 Da; a poly(2-hydroxyethyl methacrylate) (PHEMA) polymer; and a crosslinking reagent crosslinking the PEG polymer and the PHEMA polymer. In some embodiments, such polymer compositions do not comprise a block co-polymer of a PEG polymer and a PHEMA polymer.

In some embodiments, a polymer composition comprises: a polyethylene glycol (PEG) polymer, wherein the PEG polymer is derivatized with one of more functional groups selected from the group consisting of an aldehyde, an alkyne, an amine, an azide, a biotin, a carboxylic acid, a hydroxyl, a maleimide, an epoxy, an N-hydroxysuccinimide (NHS) ester, an orthopyridyl disulfide (OPSS), a sulfonate, a toluenesulfonate (tosyl), a methanesulfonate (mesyl), a 2,2,2-trifluoroethanesulfonate (tresyl), and a thiol; and a crosslinking reagent crosslinking the PEG polymer and the PHEMA polymer. In some embodiments, such polymer compositions do not comprise a block co-polymer of a PEG polymer and a PHEMA polymer.

In some embodiments, the polyethylene glycol (PEG) polymer is derivatized with one or more N-hydroxysuccinimide (NHS) esters.

In some embodiments, a polymer composition comprises: a polyethylene glycol (PEG) polymer, wherein the PEG polymer is derivatized with one of more functional groups selected from the group consisting of an aldehyde, an alkyne, an amine, an azide, a biotin, a carboxylic acid, a hydroxyl, a maleimide, an epoxy, an N-hydroxysuccinimide (NHS) ester, an orthopyridyl disulfide (OPSS), a sulfonate, a toluenesulfonate (tosyl), a methanesulfonate (mesyl), a 2,2,2-trifluoroethanesulfonate (tresyl), and a thiol, and wherein the derivatized PEG polymer has a number average molecular weight of: about 100 Daltons (Da) to about 50,000 Da; about 100 Da to about 45,000 Da; about 100 Da to about 40,000 Da; about 100 Da to about 35,000 Da, about 100 Da to about 30,000 Da; about 100 Da to about 25,000 Da; about 100 Da to about 20,000 Da; about 100 Da to about 15,000 Da; about 100 Da to about 10,000 Da; about 100 Da to about 8,000 Da, about 100 Da to about 6,000 Da; about 100 Da to about 4,000 Da; about 100 Da to about 2,000 Da; about 100 Da to about 1,000 Da; about 100 Da to about 900 Da; about 100 Da to about 800 Da; about 100 Da to about 700 Da; about 150 Da to about 700 Da; about 200 Da to about 700 Da; or about 200 Da to about 600 Da; a poly(2-hydroxyethyl methacrylate) (PHEMA) polymer, wherein the PHEMA polymer has a number average molecular weight range of: about 2,000 Daltons (Da) to about 1,000,000 Da; about 4,000 Da to about 950,000 Da; about 6,000 Da to about 900,000 Da; about 8,000 Da to about 850,000 Da, about 10,000 Da to about 800,000 Da; about 12,000 Da to about 750,000 Da; about 14,000 Da to about 700,000 Da; about 16,000 Da to about 650,000 Da; about 16,000 Da to about 600,000 Da; about 16,000 Da to about 550,000 Da, about 16,000 Daltons to about 500,000 Da; about 16,000 Da to about 450,000 Da; about 16,000 Da to about 400,000 Da; about 16,000 Da to about 350,000 Da; about 16,000 Da to about 300,000 Da; about 16,000 Daltons to about 250,000 Da; about 16,000 Da to about 200,000 Da; 16,000 Da to about 150,000 Da; about 16,000 Da to about 100,000 Da, about 16,000 Daltons to about 500,000 Da; about 16,000 Da to about 45,000 Da; about 16,000 Da to about 40,000 Da; about 16,000 Da to about 35,000 Da; about 16,000 Da to about 30,000 Da; about 16,000 Daltons to about 25,000 Da; about 16,000 Da to about 22,000 Da about 18,000 Da to about 22,000 Da; or about 18,000 Daltons to about 20,000 Da; and a crosslinking reagent crosslinking the PEG polymer and the PHEMA polymer. In some embodiments, such polymer compositions do not comprise a block co-polymer of a PEG polymer and a PHEMA polymer.

In some embodiments, a polymer composition comprises: a polyethylene glycol (PEG) polymer, wherein the PEG polymer is derivatized with ab N-hydroxysuccinimide (NHS) ester, and wherein the derivatized PEG polymer has a number average molecular weight of: about 100 Daltons (Da) to about 50,000 Da; about 100 Da to about 45,000 Da; about 100 Da to about 40,000 Da; about 100 Da to about 35,000 Da, about 100 Da to about 30,000 Da; about 100 Da to about 25,000 Da; about 100 Da to about 20,000 Da; about 100 Da to about 15,000 Da; about 100 Da to about 10,000 Da; about 100 Da to about 8,000 Da, about 100 Da to about 6,000 Da; about 100 Da to about 4,000 Da; about 100 Da to about 2,000 Da; about 100 Da to about 1,000 Da; about 100 Da to about 900 Da; about 100 Da to about 800 Da; about 100 Da to about 700 Da; about 150 Da to about 700 Da; about 200 Da to about 700 Da; or about 200 Da to about 600 Da; a poly(2-hydroxyethyl methacrylate) (PHEMA) polymer, wherein the PHEMA polymer has a number average molecular weight range of: about 2,000 Daltons (Da) to about 100,000 Da; about 4,000 Da to about 95,000 Da; about 6,000 Da to about 90,000 Da; about 8,000 Da to about 85,000 Da, about 10,000 Da to about 80,000 Da; about 12,000 Da to about 75,000 Da; about 14,000 Da to about 70,000 Da; about 16,000 Da to about 65,000 Da; about 16,000 Da to about 65,000 Da; about 16,000 Da to about 60,000 Da, about 16,000 Daltons to about 55,000 Da; about 16,000 Da to about 50,000 Da; about 16,000 Da to about 45,000 Da; about 16,000 Da to about 40,000 Da; about 16,000 Da to about 35,000 Da; about 16,000 Daltons to about 30,000 Da; about 16,000 Da to about 25,000 Da; about 18,000 Da to about 22,000 Da; or about 18,000 Daltons to about 20,000 Da; and a crosslinking reagent crosslinking the PEG polymer and the PHEMA polymer. In some embodiments, such polymer compositions do not comprise a block co-polymer of a PEG polymer and a PHEMA polymer.

In some embodiments, a polymer composition comprises the polymer composition comprises a polyethylene glycol (PEG) polymer, wherein the PEG polymer is derivatized with an N-hydroxysuccinimide (NHS) ester and wherein the derivatized PEG polymer has a molecular weight of about 600 Da; a poly(2-hydroxyethyl methacrylate) (PHEMA) polymer, wherein the PHEMA polymer has a molecular weight of about 20,000 Da; and a crosslinking reagent crosslinking the PEG polymer and the PHEMA polymer. In some embodiments, such polymer compositions do not comprise a block co-polymer of a PEG polymer and a PHEMA polymer.

In some embodiments, weight ratios of the first of the at least two hydrophilic polymers, the second of the at least two hydrophilic polymers, and the crosslinking reagent of a polymer composition may be: about 10:5:2 (w:w:w) respectively; or about (4 to 6):(2 to 3):(1 to 2) (w:w:w), respectively. In some embodiments, ratios of a PEG polymer, a PHEMA polymer, and a crosslinking agent of a polymer composition may be about: about 10:5:2 (w:w:w), respectively; or about (4 to 6):(2 to 3):(1 to 2) (w:w:w), respectively.

The term "about" as used herein and throughout is intended to qualify the numerical values which it modifies, denoting such a value as variable within a margin of error that range which would encompass the recited value and the range which would be included by rounding up or down to that figure as well, taking into account significant figures.

In some embodiments, the polymer composition comprises a crosslinking reagent represented by Formula (I):

PA-L-PA            (I)

wherein each PA is a photo-activated group or a metal-activated, and L is a linking group. In some embodiments, each PA independently comprises an azide ($-N_3$), or a diazo ($-N_2$) group. In some embodiments, each PA is the same and in other embodiments each PA is different. In some embodiments PA is photo-activated or metal-activated to form a nitrene intermediate capable of C—H and/or O—H insertion. See, for example, "Photogenerated reactive intermediates and their properties," Chapter 2 in *Laboratory Techniques in Biochemistry and Molecular Biology*, Elsevier Press, 12:8-24 (1983). In some embodiments, PA is metal activated to form a carbene or carbenoid intermediate capable of C—H and/or O—H insertion. See, for example, Doyle et al. "Catalytic Carbene Insertion into C—H Bonds," *Chem. Rev.* 2:704-724 (2010).

In some embodiments, each PA is an azide ($-N_3$) moiety and photoactivation generates nitrene intermediates capable of C—H and/or O—H insertion thereby mediating crosslinking of PEG and PHEMA polymers. In some embodiments, each PA is a diazo ($-N_2$) and metal catalyzed decomposition reaction forms a carbene or carbenoid intermediate capable of C—H and/or O—H insertion thereby mediating crosslinking of PEG and PHEMA polymers. Both azide and diazo preparations are well known in the art, and in the case of azide are readily prepared by $S_N^2$ displacement reaction of azide anion, $N_3^-$ with an appropriate organic moiety possessing a leaving group.

In some embodiments, L in Formula (I) can be any organic fragment that will support the presence of many PA moieties on one L. In some embodiments, the L may be a hydrocarbon, including a hydrocarbon that is linear, branched, cyclic, or a combination thereof; aromatic, non-aromatic, or a combination thereof; monocyclic, polycyclic, carbocyclic, heterocyclic, or a combination thereof; benzene or a derivative thereof; or combinations thereof. L can be a simple $C_2$-$C_{20}$ hydrocarbon chain that is straight chained or branched. In some embodiments, L is a $C_2$-$C_6$ straight chain alkyl group. Any of the foregoing hydrocarbons can include fluorinated variants with any degree of fluorine substitution. In some embodiments, L can include aromatic hydrocarbons including, without limitation, benzene, naphthalene, biphenyl, binaphthyl, or combinations of aromatic structures with $C_2$-$C_{20}$ hydrocarbon chains. Thus, in some embodiments, L can be alkyl, aryl, or aralkyl in structure. In some embodiments, alkyl linking groups may have one or more carbons in their chains substituted with oxygen (O), or an amine (NR), where R is H or $C_1$-$C_6$ alkyl. In some embodiments, the linking groups may comprise one or more unsaturations and thus include one or more alkenyl and/or alkynyl moieties.

In some embodiments, L comprises at least one Y and at least one X. In some embodiments, each at least one Y is independently selected from the group consisting of: an optionally substituted divalent alkylene; an optionally substituted arylene; and optionally substituted divalent heteroaromatic ring moiety; having from 1 to 20 atoms.

In some embodiments, each at least on Y is, independently: an alkylene, $-(CR_2)_p-$, wherein p is an integer from 1 to 10, 1 to 6, or 1 to 4, and wherein $R_2$ is independently selected from the group consisting of H and lower alkyl, $C_1$-$C_5$ alkyl, and $C_1$-$C_3$ alkyl.

In some embodiments, each at least on Y is, independently, an arylene.

In some embodiments, each at least on Y is, independently, a divalent heteroaromatic ring having from 4 to 20 carbon atoms and contains at least one heteroatom selected from the group consisting of O, N, and S.

In some embodiments, each at least one X is, independently, selected from the group consisting of alkylene, $-NR_1-$, $-O-$, $-S-$, $-S-S-$, $-CO-NR_1-$, $-NR_1-CO-$, $-CO-O-$, $-O-CO-$, $-CO-$, and a bond, wherein $R_1$ is independently selected from the group consisting of H and lower alkyl.

In some embodiments, each of the at least one Y and each of the at least one X are, independently, optionally substituted.

In some embodiments, one or more of the at least one X are the same.

In certain embodiments, one or more of the at least one Y are the same.

In certain embodiments, one or more the at least one X are different.

In certain embodiments, one or more the at least one are different.

The term "alkyl," as used herein, alone or in combination, refers to a straight-chain or branched-chain alkyl radical containing from 2 to 20 carbon atoms. In some embodiments, the alkyl may comprise from 2 to 10 carbon atoms. In further embodiments, the alkyl group may comprise from 2 to 6 carbon atoms. Alkyl groups may be optionally substituted as defined herein below. Examples of alkyl group (given as radicals) include, without limitation methyl, ethyl, n-propyl, isopropyl, n-butyl, isobutyl, sec-butyl, tert-butyl, pentyl, iso-amyl, hexyl, octyl, nonyl and the like.

The term "alkenyl," as used herein, alone or in combination, refers to a straight-chain or branched-chain hydrocarbon radical having one or more double bonds and containing from 2 to 20 carbon atoms. In some embodiments, the alkenyl group may comprise from 2 to 6 carbon atoms.

The term "alkenylene" refers to a carbon-carbon double bond system attached at two or more positions such as ethenylene [($-CH=CH-$), ($-C::C-$)]. Examples of suitable alkenyl radicals include propenyl, 2-methylpropenyl, 1,4-butadienyl and the like.

The term "alkynyl," as used herein, alone or in combination, refers to a straight-chain or branched chain hydrocarbon radical having one or more triple bonds and containing from 4 to 20 carbon atoms. In certain embodiments, said alkynyl comprises from 4 to 6 carbon atoms. Examples of alkynyl groups include butyn-1-yl, butyn-2-yl, pentyn-1-yl, 3-methylbutyn-1-yl, hexyn-2-yl, and the like.

The term "aryl," as used herein, alone or in combination, means a carbocyclic aromatic system containing one, two or three rings wherein such rings may be attached together in a pendent manner or may be fused. In some embodiments, "Aryl" groups include groups having one or more 5- or 6-member aromatic rings. Aryl groups contain no heteroatoms in the aryl rings. Aryl groups are optionally substituted with one or more non-hydrogen substituents.

The term "aryl" embraces aromatic radicals such as benzyl, phenyl, naphthyl, anthracenyl, phenanthryl, indanyl, indenyl, annulenyl, azulenyl, tetrahydronaphthyl, and biphenyl.

The term "arylene," refers to a divalent aromatic radical which consists of the elements carbon and hydrogen. The divalent aromatic radical may include only one benzene ring, or a plurality of benzene rings as in diphenyl, naphthyl, oranthracyl.

The term "aralkyl," as used herein, alone or in combination, refers to an aryl group attached to the parent molecular moiety through an alkyl group.

The term "heteroaryl" and "heteroaromatic rings", as used herein, refer to and include groups having one or more aromatic rings in which at least one ring contains a heteroatom (a non-carbon ring atom). Heteroaryl groups include those having one or two heteroaromatic rings carrying 1, 2 or 3 heteroatoms. Heteroaryl groups can contain 5-20, 5-12 or 5-10 ring atoms. Heteroaryl groups include those having one aromatic ring contains a heteroatom and one aromatic ring containing carbon ring atoms. Heteroaryl groups include those having one or more 5- or 6-member aromatic heteroaromatic rings and one or more 6-member carbon aromatic rings. Heteroaromatic rings can include one or more N, O, or S atoms in the ring. Heteroaromatic rings can include those with one, two or three N, those with one or two O, and those with one or two S, or combinations of one or two or three N, O or S. Specific heteroaryl groups include furyl, pyridinyl, pyrazinyl, pyrimidinyl, quinolinyl, and purinyl groups.

The term "lower alkyl" refers to, for example, $C_1$-$C_9$ alkyl, $C_1$-$C_8$ alkyl, $C_1$-$C_7$ alkyl, $C_1$-$C_6$ alkyl, $C_1$-$C_6$ alkyl, $C_1$-$C_5$ alkyl, $C_1$-$C_4$ alkyl, $C_1$-$C_3$ alkyl, or $C_1$-$C_2$ alkyl.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., $-CH_2CH_3$), fully substituted (e.g., $-CF_2CF_3$), monosubstituted (e.g., $-CH_2CH_2F$) or substituted at a level anywhere in-between fully substituted and monosubstituted (e.g., $-CH_2CF_3$). Where substituents are recited without qualification as to substitution, both substituted and unsubstituted forms are encompassed.

Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with." The term "lower," as used herein, alone or in combination, means containing from 1 to and including 6 carbon atoms.

In some embodiments, the polymer composition comprises a crosslinking reagent represented by Formula (I):

$$PA\text{-}L\text{-}PA \qquad (I)$$

wherein L is a linking group and each PA independently comprises an azide ($-N_3$), a diazo ($-N_2$) group, an aryl azide, an acyl azide, an azidoformate, a sulfonyl azide, a phosphoryl azide, a diazoalkane, a diazoketone, a diazoacetate, a diazirine, an aliphatic azo, an aryl ketone, benzophenone, acetophenone, anthroquinone, or an anthrone.

In some embodiments, each PA independently comprises an azide ($-N_3$), or a diazo ($-N_2$) group.

In some embodiments, the polymer composition comprises a crosslinking reagent represented by Formula (I):

$$PA\text{-}L\text{-}PA \qquad (I)$$

wherein each PA independently comprises an azide ($-N_3$), a diazo ($-N_2$) group, an aryl azide, an acyl azide, an azidoformate, a sulfonyl azide, a phosphoryl azide, a diazoalkane, a diazoketone, a diazoacetate, a diazirine, an aliphatic azo, an aryl ketone, benzophenone, acetophenone, anthroquinone, and anthrone;

L comprises at least one Y and one or more X, wherein:

a) each at least one Y is independently selected from the group consisting of: an optionally substituted divalent alkylene; an optionally substituted arylene; and optionally substituted divalent heteroaromatic ring moiety; having from 1 to 20 atoms; an alkylene, $-(CR_2)_p-$, wherein p is an integer from 1 to 10, 1 to 6, or 1 to 4, and wherein $R_2$ is independently selected from the group consisting of H and lower alkyl, $C_1$-$C_5$ alkyl, and $C_1$-$C_3$ alkyl; and/or a divalent heteroaromatic ring having from 4 to 20 carbon atoms and contains at least one heteroatom selected from the group consisting of O, N, and S; and b) each X is independently selected from the group consisting of alkylene, $-NR_1-$, $-O-$, $-S-$, $-S-S-$, $-CO-NR_1-$, $-NR_1-CO-$, $-CO-O-$, $-O-CO-$, $-CO-$, and a bond, wherein $R_1$ is independently selected from the group consisting of H and lower alkyl.

In some embodiments, the polymer composition comprises a crosslinking reagent represented by Formula (II):

$$PA\text{-}Y_1\text{-}X_1\text{-}X_2\text{-}X_3\text{-}X_4\text{-}X_5\text{-}X_6\text{-}X_7\text{-}X_8\text{-}X_9\text{-}Y_2\text{-}PA \qquad (II)$$

wherein each PA is a photo-activated group or a metal-activated group, and $Y_1$-$X_1$-$X_2$-$X_3$-$X_4$-$X_5$-$X_6$-$X_7$-$X_8$-$X_9$-$Y_2$ is a linking group, wherein; each PA, independently, comprises an azide ($-N_3$), a diazo ($-N_2$) group, an aryl azide, an acyl azide, an azidoformate, a sulfonyl azide, a phosphoryl azide, a diazoalkane, a diazoketone, a diazoacetate, a diazirine, an aliphatic azo, an aryl ketone, benzophenone, acetophenone, anthroquinone, and anthrone. In some embodiments, each PA independently comprises an azide ($-N_3$), or a diazo ($-N_2$) group.

In some embodiments, $Y_1$ and $Y_2$ are each, independently: an alkylene, $-(CR_2)p-$, wherein p is an integer from 1 to 10, 1 to 6, or 1 to 4, and wherein $R_2$ is independently selected from the group consisting of H and lower alkyl, $C_1$-$C_5$ alkyl, and $C_1$-$C_3$ alkyl.

In some embodiments, $Y_1$ and $Y_2$ are each, independently, an arylene.

In some embodiments, $Y_1$ and $Y_2$ are each, independently, a divalent heteroaromatic ring having from 4 to 20 carbon atoms and contains at least one heteroatom selected from the group consisting of O, N, and S.

In some embodiments, $X_1$, $X_2$, $X_3$, $X_4$, $X_5$, $X_6$, $X_7$, $X_8$, and $X_9$ are each, independently, selected from the group consisting of alkylene, $-NR_1-$, $-O-$, $-S-$, $-S-S-$, $-CO-NR_1-$, $-NR_1-CO_2-$, $-CO-O-$, —O—CO—, —CO—, and a bond, wherein $R_1$ is independently selected from the group consisting of H and lower alkyl.

In some embodiments, each of $Y_1$ and $Y_2$, $X_1$, $X_2$, $X_3$, $X_4$, $X_5$, $X_6$, $X_7$, $X_8$, and $X_9$ are, independently, optionally substituted.

In some embodiments, one or more of $X_1$, $X_2$, $X_3$, $X_4$, $X_5$, $X_6$, $X_7$, $X_8$, and $X_9$ are the same.

In certain embodiments, $Y_1$ and $Y_2$ are the same.

In certain embodiments, one or more $X_1$, $X_2$, $X_3$, $X_4$, $X_5$, $X_6$, $X_7$, $X_8$, and $X_9$ is different.

In certain embodiments, $Y_1$ and $Y_2$ are different.

In some embodiments, the polymer composition comprises a crosslinking reagent represented by Formula (II):

$$PA\text{-}Y_1\text{-}X_1\text{-}X_2\text{-}X_3\text{-}X_4\text{-}X_5\text{-}X_6\text{-}X_7\text{-}X_8\text{-}X_9\text{-}Y_2\text{-}PA \qquad (II)$$

wherein each PA is a photo-activated group or a metal-activated group, and $Y_1\text{-}X_1\text{-}X_2\text{-}X_3\text{-}X_4\text{-}X_5\text{-}X_6\text{-}X_7\text{-}X_8\text{-}X_9\text{-}Y_2$ is a linking group, wherein; each PA, independently, comprises an azide ($—N_3$), a diazo ($—N_2$) group, an aryl azide, an acyl azide, an azidoformate, a sulfonyl azide, a phosphoryl azide, a diazoalkane, a diazoketone, a diazoacetate, a diazirine, an aliphatic azo, an aryl ketone, benzophenone, acetophenone, anthroquinone, and anthrone;

(a) $Y_1$ and $Y_2$ are each, independently, selected from the group consisting of: an optionally substituted divalent alkylene; an optionally substituted arylene; and optionally substituted divalent heteroaromatic ring moiety; having from 1 to 20 atoms; an alkylene, $—(CR_2)_p—$, wherein p is an integer from 1 to 10, 1 to 6, or 1 to 4, and wherein $R_2$ is independently selected from the group consisting of H and lower alkyl, $C_1\text{-}C_5$ alkyl, and $C_1\text{-}C_3$ alkyl; and/or a divalent heteroaromatic ring having from 4 to 20 carbon atoms and contains at least one heteroatom selected from the group consisting of O, N, and S; and c) each of $X_1$, $X_2$, $X_3$, $X_4$, $X_5$, $X_6$, $X_7$, $X_8$, and $X_9$ is independently selected from the group consisting of alkylene, —O—, —S—, —S—S—, —CO—$NR_1$—, —$NR_1$—CO—, —CO—O—, —O—CO—, —CO—, and a bond, wherein $R_1$ is independently selected from the group consisting of H and lower alkyl.

In some embodiments, provided are polymer compositions comprising: a polyethylene glycol (PEG) polymer; a poly(2-hydroxyethyl methacrylate) (PHEMA) polymer; and a crosslinking reagent represented by either Formula (I) or Formula (II).

In some embodiments, the crosslinking reagent comprises bis[2-(4-azidosalicylamido)ethyl]disulfide or dithiobis(phenylazide).

In some embodiments, a polymer composition comprises: a polyethylene glycol (PEG) polymer; a poly(2-hydroxyethyl methacrylate) (PHEMA) polymer; and a crosslinking reagent represented by Formula (I):

$$PA\text{-}L\text{-}PA \qquad (I)$$

wherein:
    each PA independently comprises an azide ($—N_3$), a diazo ($—N_2$) group, an aryl azide, an acyl azide, an azidoformate, a sulfonyl azide, a phosphoryl azide, a diazoalkane, a diazoketone, a diazoacetate, a diazirine, an aliphatic azo, an aryl ketone, benzophenone, acetophenone, anthroquinone, and anthrone;
    L comprises at least one Y and one or more X, wherein:
        a) each at least one Y is independently selected from the group consisting of: an optionally substituted divalent alkylene; an optionally substituted arylene; and optionally substituted divalent heteroaromatic ring moiety; having from 1 to 20 atoms; an alkylene, $—(CR_2)_p—$, wherein p is an integer from 1 to 10, 1 to 6, or 1 to 4, and wherein $R_2$ is independently selected from the group consisting of H and lower alkyl, $C_1\text{-}C_5$ alkyl, and $C_1\text{-}C_3$ alkyl; and/or a divalent heteroaromatic ring having from 4 to 20 carbon atoms and contains at least one heteroatom selected from the group consisting of O, N, and S; and b) each X is independently selected from the group consisting of alkylene, —$NR_1$—, —O—, —S—, —S—S—, —CO—$NR_1$—, —$NR_1$—CO—, —CO—O—, —O—CO—, —CO—, and a bond, wherein $R_1$ is independently selected from the group consisting of H and lower alkyl.

In some embodiments, the crosslinking reagent comprises bis[2-(4-azidosalicylamido)ethyl]disulfide or dithiobis(phenylazide).

In some embodiments, a polymer composition comprises: a polyethylene glycol (PEG) polymer; a poly(2-hydroxyethyl methacrylate) (PHEMA) polymer; and a crosslinking reagent represented by Formula (II):

$$PA\text{-}Y_1\text{-}X_1\text{-}X_2\text{-}X_3\text{-}X_4\text{-}X_5\text{-}X_6\text{-}X_7\text{-}X_8\text{-}X_9\text{-}Y_2\text{-}PA \qquad (II)$$

wherein each PA is a photo-activated group or a metal-activated group, and $Y_1\text{-}X_1\text{-}X_2\text{-}X_3\text{-}X_4\text{-}X_5\text{-}X_6\text{-}X_7\text{-}X_8\text{-}X_9\text{-}Y_2$ is a linking group, wherein:
    each PA independently comprises an azide ($—N_3$), a diazo ($—N_2$) group, an aryl azide, an acyl azide, an azidoformate, a sulfonyl azide, a phosphoryl azide, a diazoalkane, a diazoketone, a diazoacetate, a diazirine, an aliphatic azo, an aryl ketone, benzophenone, acetophenone, anthroquinone, and anthrone;
    each of $Y_1$, and $Y_2$ is independently selected from the group consisting of: an optionally substituted divalent alkylene; an optionally substituted arylene; and optionally substituted divalent heteroaromatic ring moiety; having from 1 to 20 atoms; an alkylene, $—(CR_2)_p—$, wherein p is an integer from 1 to 10, 1 to 6, or 1 to 4, and wherein $R_2$ is independently selected from the group consisting of H and lower alkyl, $C_1\text{-}C_5$ alkyl, and $C_1\text{-}C_3$ alkyl; and/or a divalent heteroaromatic ring having from 4 to 20 carbon atoms and contains at least one heteroatom selected from the group consisting of O, N, and S; and
    each of $X_1$, $X_2$, $X_3$, $X_4$, $X_5$, $X_6$, $X_7$, $X_8$, and $X_9$ is independently selected from the group consisting of alkylene, —O—, —S—, —S—S—, —CO—$NR_1$—, —$NR_1$—CO—, —CO—O—, —O—CO—, —CO—, and a bond, wherein $R_1$ is independently selected from the group consisting of H and lower alkyl. In some embodiments, the crosslinking reagent comprises bis [2-(4-azidosalicylamido)ethyl]disulfide or dithiobis (phenylazide).

In some embodiments, the PEG polymer is derivatized with an N-hydroxysuccinimide (NHS) ester and wherein the derivatized PEG polymer has a molecular weight of about 600 Da.

In some embodiments, there are provided polymer compositions disposed as a layer on a sensor as a biosurface prepared by a method comprising crosslinking the at least two hydrophilic polymers of the polymer composition with the crosslinking reagent via an attachment atom.

In some such embodiments, the crosslinking agent is represented by each A in Formula (I) or Formula (II).

In some such embodiments, each A in Formula (I) and Formula (II) represents an attachment atom derived from the decomposition reaction of an azide ($—N_3$), a diazo ($—N_2$)

group, an aryl azide, an acyl azide, an azidoformate, a sulfonyl azide, a phosphoryl azide, a diazoalkane, a diazoketone, a diazoacetate, a diazirine, an aliphatic azo, an aryl ketone, benzophenone, acetophenone, anthroquinone, or an anthrone.

In addition to compounds of Formula (I) and Formula (II), other compounds that may serve as crosslinkers include, without limitation, the crosslinkers disclosed in U.S. Pat. Nos. 10,315,987, 10,253,193, 9,994,721, 9,487,663, and 8,889,760, all of which are incorporated herein by reference in their entirety.

In some embodiments, provided are biosurfaces comprising a polymer composition disposed as a layer on a sensor, wherein the biosurface is prepared by a method comprising crosslinking at least two hydrophilic polymers of the polymer composition with the crosslinking reagent. In some embodiments, the crosslinking comprises a decomposition reaction of an attachment atom on the crosslinking reagent. In some embodiments, the decomposition reaction occurs by a method comprising photocatalysis. In some embodiments, the decomposition reaction occurs by a method comprising metal catalysis. In one or more of the preceding embodiments, the crosslinking is photocatalyzed. In some embodiments, the photocatalysis comprises irradiating the polymer composition with for example, ultraviolet light (i.e., light has a wavelength in the ultraviolet wavelength range).

In some embodiments, provided is a biosurface comprising a polymer composition of any disposed as a layer on a sensor, wherein said biosurface is prepared by a method comprising by crosslinking at least two hydrophilic polymers with a crosslinking reagent represented by Formula (I) or Formula (II), wherein each A is an attachment atom derived from the decomposition reaction of an azide ($-N_3$), a diazo ($-N_2$) group, an aryl azide, an acyl azide, an azidoformate, a sulfonyl azide, a phosphoryl azide, a diazoalkane, a diazoketone, a diazoacetate, a diazirine, an aliphatic azo, an aryl ketone, benzophenone, acetophenone, anthroquinone, or an anthrone. In some embodiments, the crosslinking comprises a decomposition reaction of an attachment atom on the crosslinking reagent. In some embodiments, the decomposition reaction occurs by a method comprising photocatalysis. In some embodiments, the decomposition reaction occurs by a method comprising metal catalysis. In one or more of the preceding embodiments, the crosslinking is photocatalyzed. In some embodiments, the photocatalysis comprises irradiating the polymer composition with for example, ultraviolet light (i.e., light has a wavelength in the ultraviolet wavelength range).

In some embodiments, a polymer composition and/or a biosurface further comprises a covalently attached biomolecule. In some such embodiments, the covalently attached molecule comprises a covalently attached biomolecule comprising a protein, a transcription factor, a nucleic acid, a deoxyribonucleic acid, a ribonucleic acid, a polynucleotide, a double-stranded DNA (dsDNA), a single stranded DNA (ssDNA), a hybrid double-stranded polynucleotide comprising a ssDNA and a ssRNA, an oligonucleotide, a carbohydrate, a hormone, a glycoprotein, an immunoglobulins, an antibody, or antigen-binding antibody fragments.

In some such embodiments, the covalently attached molecule is a protein.

In some such embodiments, the covalently attached biomolecule comprises an antibody, an immunoglobulin, or an antigen-binding antibody fragment.

In some such embodiments, the covalently attached molecule comprises a double-stranded DNA (dsDNA).

The term "nucleic acid" refers, in addition to the nucleic acids disclosed above, complementary DNA (cDNA), genomic DNA (gDNA), and the like, and/or messenger ribonucleic acid (mRNA), short inhibitory RNA (siRNA), DNA or RNA analogs (e.g., containing base analogs, sugar analogs and/or a non-native backbone and the like), RNA/DNA hybrids and polyamide nucleic acids (PNAs), the like and combinations thereof. Nucleic acids can be single- or double-stranded. In some embodiments, a nucleic acid is a primer. In some embodiments, a nucleic acid is a target nucleic acid. A target nucleic acid is often a nucleic acid of interest.

In one or more of the preceding embodiments, the PEG polymer further comprises one or two terminal N-hydroxysuccinimide (NHS) groups.

In one or more of the preceding embodiments, at least one of the at least two hydrophilic polymers is provided in a solvent. In one or more of the preceding embodiments, a PEG polymer and/or a PHEMA polymer is provided in a solvent. In one or more of the preceding embodiments, the solvent is isopropyl alcohol, water, or mixtures thereof.

In some embodiments, there are provided methods of forming a biosurface on a sensor comprising coating the sensor with at least two hydrophilic polymers and a crosslinking reagent as disclosed herein. In some embodiments, methods comprise forming a biosurface on a sensor comprising coating the sensor with at least one hydrophilic polymer selected from the group consisting of a polyethylene glycol (PEG) polymer, a cellulose, a starch, a chitin, and alginate, and a dextran, and at least one poly(2-hydroxyethyl methacrylate) (PHEMA) polymer. In some embodiments, one hydrophilic polymer comprises a PEG polymer and another of the at least two hydrophilic polymers comprises a PHEMA polymer.

In some embodiments, there are provided methods of forming a biosurface on a sensor comprising coating the sensor with at least two hydrophilic polymers and a crosslinking reagent represented by Formula (I) or Formula (II).

In some embodiments, hydrophilic polymers and the crosslinking reagent are mixed together in a solvent, and the coating step of each is simultaneous. In some embodiments, the hydrophilic polymers and the crosslinking reagent are each provided in a separate solvent, and the coating step of each is performed sequentially. In one or more of the preceding embodiments, the solvent is selected from the group consisting of isopropyl alcohol, water, and mixtures thereof. In some embodiments, other solvents such as methanol, acetone may be employed. In some embodiments, one or more of the hydrophilic polymers and the crosslinking reagent are provided as a solid, for example, a powder, and is dissolved in a solvent.

In some embodiments, one hydrophilic polymer is coated first on a sensor, then the crosslinking reagent, then the other hydrophilic polymer. In some embodiments, a PEG polymer is coated first on a sensor, then a crosslinking reagent, then a PHEMA polymer. In some embodiments, a PHEMA polymer is coated first on a sensor, then a crosslinking reagent, then a PEG polymer. In some embodiments, a PEG polymer is coated first on a sensor, then a crosslinking reagent, then a PHEMA polymer. In some embodiments, coating of sensors may be performed by any combination or permutation of the above.

In some embodiments, the coating step comprises microprinting. As a non-limiting example, a sensor or other substrate may be coated with a PEG polymer, PHEMA polymer, and/or crosslinking reagent via non-contact capillary dispensing or contact printing. The thickness of the component may be controlled by the number of drops and/or drop volume from the dispensing capillary.

In some embodiments, a coating step comprises dip coating. As a non-limiting example, a sensor or other substrate may be dipped into a container of any or all of a PEG polymer, a PHEMA polymer, and/or a crosslinking reagent. The desired sensor area or surface is submerged in a solution of these components and then removed. Thickness may be controlled by the speed of the dip and removal process.

In some embodiments, the coating step comprises spin coating. As a non-limiting example, any or all of a PEG polymer, a PHEMA polymer, and/or a crosslinking reagent may be deposited onto a sensor or other substrate by attachment of the sensor or substrate to a spin coater, with the aid of vacuum suction or other fixture. The sensor or substrate is spun while the polymer composition components are deposited. The thickness of the deposition may be controlled by speed and time of spinning and the volume of the polymer composition components.

In some embodiments, the coating step comprises aerosol coating. As a non-limiting example, aerosol coating equipment may be loaded with any or all of a PEG polymer, a PHEMA polymer, and/or a crosslinking reagent and used to coat the sensor or other substrate.

In some embodiments, for example, when individual polymer composition components are added sequentially, any combination of the aforementioned coating techniques may be employed for each of the polymers and/or the crosslinking reagent.

In some embodiments, after coating, the polymer composition may be crosslinked. In some embodiments, the crosslinking is photocatalyzed. In one or more of the preceding embodiments, the crosslinking is metal-catalyzed. In one or more of the preceding embodiments, photocatalyzed crosslinking may employ UV radiation. Following crosslinking the surface may be washed with solvent such as isopropyl alcohol, water or mixtures thereof.

In one or more of the preceding embodiments, methods may further comprise attaching a biomolecule to form the biosurface.

In one or more of the preceding embodiments, a thickness of the formed biosurface may vary from about 5 nm to about 5 microns.

EXAMPLES

Example 1: Biosurface Preparation

Five polymer compositions were prepared. Each polymer composition was prepared using 7.5 mg/ml of a PHEMA having a molecular weight of approximately 22,000 Daltons (Da), 5 mg/ml of polyethylene glycol (PEG)-N-hydroxysuccinimide (NHS) having a molecular weight of approximately 600 Da, and either 0.05 mg/mL 0.1 mg/mL, 0.2 mg/mL, 0.3 mg/mL, or 0.5 mg/mL dithiobis(phenylazide), respectively. Each polymer composition was prepared in isopropyl alcohol. Thus, each polymer solution differed only in the concentration of dithiobis(phenylazide) as outlined above.

Five clean glass slides were each dip-coated by dipping each of the slides into one of the polymer compositions prepared in step 1, so that one dip-coated slide was prepared from each of the five polymer compositions. Each glass slide was dipped in the respective polymer composition at a rate of 5 millimeters/second and removed from the polymer composition at a rate of 2 millimeters/second.

Each dip-coated slide was then cured by exposing the dip-coated slide to UV-A light with a peak wavelength of 365 nanometers and an intensity of 70 mW/cm2 for 90 seconds.

Each cured slide was then washed first with water, then with isopropyl alcohol, then with water again. Each cured slide was then dried with nitrogen.

A DNA oligonucleotide with a cyanine 3 and amino placed at the 5' and 3' ends of the oligonucleotide (Cy3-DNA-NH2) was printed onto the surface of each cured slide. The printed slide was then incubated for 2 hours at room temperature and 50% relative humidity, thereby drying and immobilizing each printed slide.

After drying and immobilizing each printed slide, the slides were each washed with SSC buffer to remove unbound Cy3-DNA-NH2, then rinsed with water, and then finally dried.

Example 2: Biosurface Performance Results

Figure 2B:
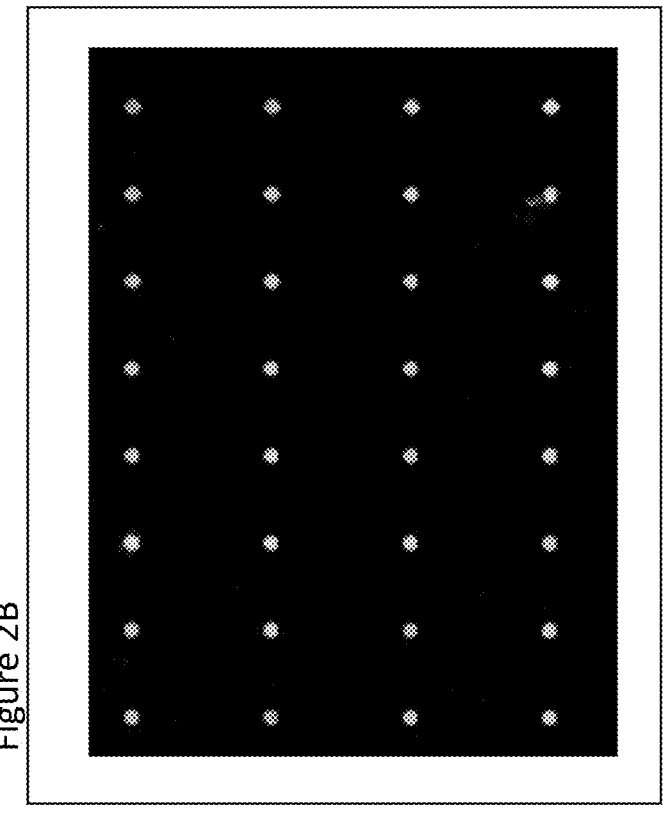
FIGS. 2A and 2B depicts the results described in the Examples.
Figure 2A:
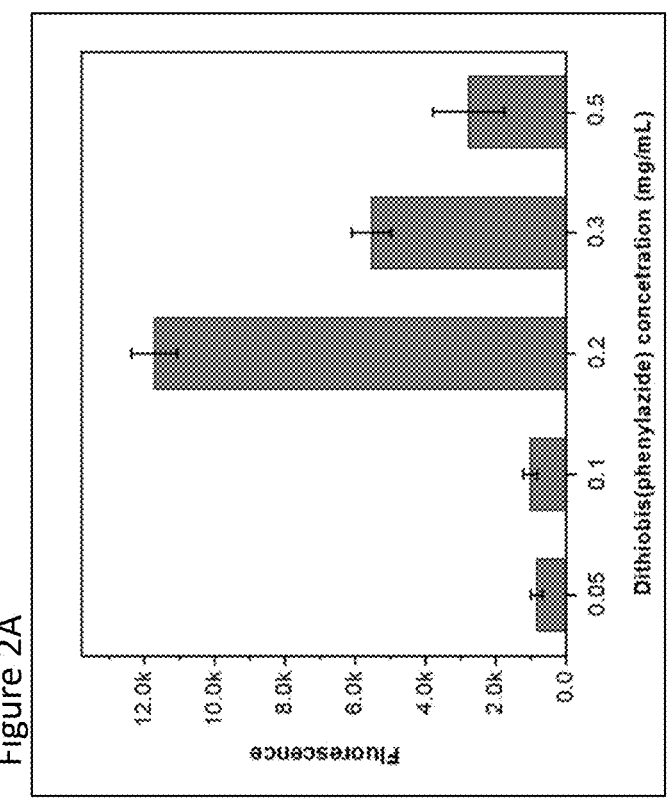
Figure 3:
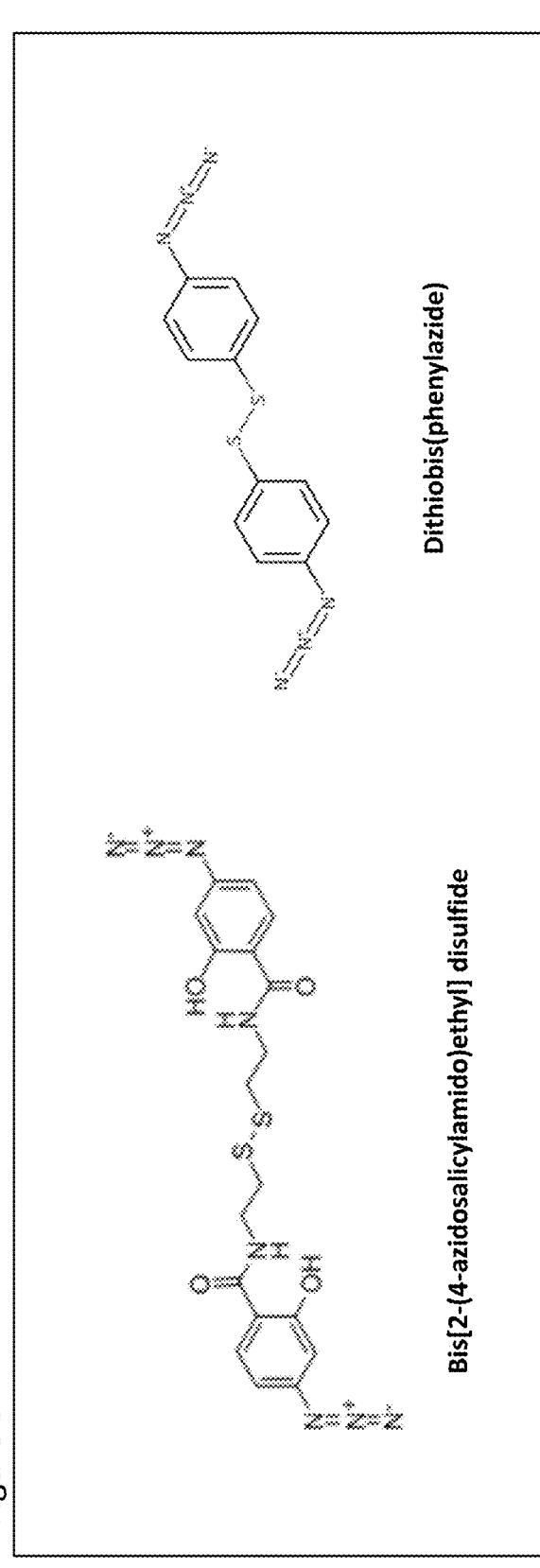
FIG. 3 provides the chemical structures of two exemplary crosslinking reagents.

Each biosurface slide was scanned and analyzed using a GenePix® Professional 4200A microarray scanner. The results, depicted in FIG. 2A, demonstrate that each biosurface prepared as described above generated a detectable fluorescence signal from approximately 1,000 to approximately 12,000. Biosurface slides prepared using 0.05 mg/mL, 0.1 mg/mL, 0.2 mg/mL, 0.3 mg/mL, and 0.5 mg/mL dithiobis(phenylazide) yielded fluorescence signals of approximately 900, 1,000, 12,000, 6,000, and 3,000, respectively. A fluorescence microarray image of the slide biosurface prepared as described above using 0.2 mg/mL dithiobis (phenylazide) is depicted in FIG. 2B.

It is to be understood that all embodiments disclosed herein may be combined in any manner to carry out a method of detecting an analyte and that such methods may be carried out using any combination of embodiments disclosed herein describing the various system components.

While the principles of the disclosure have been made clear in the illustrative embodiments set forth above, it will be apparent to those skilled in the art that various modifications may be made to the structure, arrangement, proportion, elements, materials, and components used in the practice of the disclosure.

It will thus be seen that the features of this disclosure have been fully and effectively accomplished. It will be realized, however, that the foregoing preferred specific embodiments have been shown and described for the purpose of illustrating the functional and structural principles of this disclosure and are subject to change without departure from such principles. Therefore, this disclosure includes all modifications encompassed within the spirit and scope of the following claims.

What is claimed is:

1. A polymer composition comprising:
    a polyethylene glycol (PEG) polymer having a molecular weight from about 100 Da to about 10,000 Da, a poly(2-hydroxyethyl methacrylate) (PHEMA) polymer having a molecular weight of about 16,000 Da to about 1,000,000 Da;
    and a crosslinking reagent that crosslinks polymers.

2. The polymer composition of claim 1, wherein the composition further comprises a polysaccharide that is selected from the group consisting of a cellulose, a starch, a chitin, and alginate, and a dextran.

3. The polymer composition of claim 1, wherein the PEG polymer has a molecular weight of about 100 Da to about 1,000 Da.

4. The polymer composition of claim 1, wherein the PEG polymer is derivatized with one or more functional groups selected from the group consisting of an aldehyde, an alkyne, an amine, an azide, a biotin, a carboxylic acid, a hydroxyl, a maleimide, an epoxy, an N-hydroxysuccinimide (NHS) ester, an orthopyridyl disulfide (OPSS), a sulfonate, a toluenesulfonate (tosyl), a methanesulfonate (mesyl), a 2,2,2-trifluoroethanesulfonate (tresyl), and a thiol.

5. The polymer composition of claim 1, wherein the polyethylene glycol (PEG) polymer is derivatized with one or more N-hydroxysuccinimide (NHS) esters.

6. The polymer composition of claim 3, wherein the PHEMA polymer has a molecular weight range of about 16,000 Da to about 45,000 Da.

7. The polymer composition of claim 1, wherein the crosslinking reagent is represented by Formula (I):

PA-L-PA        (I)

wherein each PA is independently selected from a photo-activated group or a metal-activated group, and L is a linking group.

8. The polymer composition of claim 7, wherein each PA independently comprises an azide ($-N_3$), a diazo ($-N_2$) group, an aryl azide, an acyl azide, an azidoformate, a sulfonyl azide, a phosphoryl azide, a diazoalkane, a diazoketone, a diazoacetate, a diazirine, an aliphatic azo, an aryl ketone, benzophenone, acetophenone, anthraquinone, and anthrone.

9. The polymer composition of claim 8, wherein each PA independently comprises an azide ($-N_3$), or a diazo ($-N_2$) group.

10. The polymer composition of claim 7, wherein L comprises at least one Y and one or more X, wherein:
  a) each at least one Y is independently selected from the group consisting of: an optionally substituted divalent alkylene; an optionally substituted arylene; and optionally substituted divalent heteroaromatic ring moiety; having from 1 to 20 atoms; an alkylene, $-(CR_2)_p-$, wherein p is an integer from 1 to 10, 1 to 6, or 1 to 4, and wherein $R_2$ is independently selected from the group consisting of H and lower alkyl, $C_1$-$C_5$ alkyl, and $C_1$-$C_3$ alkyl; and/or a divalent heteroaromatic ring having from 4 to 20 carbon atoms and contains at least one heteroatom selected from the group consisting of O, N, and S; and
  b) each X is independently selected from the group consisting of alkylene, $-NR_1-$, $-O-$, $-S-$, $-S-S-$, $-CO-NR_1-$, $-NR_1-CO-$, $-CO-O-$, $-O-CO-$, $-CO-$, and a bond, wherein $R_1$ is independently selected from the group consisting of H and lower alkyl.

11. The polymer composition of claim 10, wherein said crosslinking reagent is represented by Formula (II):

PA-$Y_1$-$X_1$-$X_2$-$X_3$-$X_4$-$X_5$-$X_6$-$X_7$-$X_8$-$X_9$-$Y_2$-PA     (II)

wherein each PA is a photo-activated group or a metal-activated group, and $Y_1$-$X_1$-$X_2$-$X_3$-$X_4$-$X_5$-$X_6$-$X_7$-$X_8$-$X_9$-$Y_2$ is a linking group.

12. The polymer composition of claim 1, wherein the crosslinking reagent comprises bis[2-(4-azidosalicylamido)ethyl]disulfide or dithiobis(phenylazide).

13. The polymer composition of claim 1, wherein the composition further comprises a branched polyethylene glycol (PEG) polymer.

14. The polymer composition of claim 13, wherein the branched PEG polymer comprises 4-arm PEG, 8-arm PEG, 4-arm PEG-OH, 8-arm PEG-OH, 4-arm PEG-acrylate, 8-arm PEG-acrylate, 4-arm PEG-acrylamide, 8-arm PEG-acrylamide, 4-arm PEGamine, 8-arm PEG-amine, 4-arm PEG-thiol, 8-arm PEG thiol, 4-arm PEG maleimide, 8-arm PEG maleimide, 4-arm PEG-succinimidyl carboxymethyl ester (NHS), 8-arm PEG-succinimidyl carboxymethyl ester (NHS), 4-arm PEG-succinimidyl glutarate ester, 8-arm PEG-succinimidyl glutarate ester, 4-arm PEG-succinimidyl succinate ester, 8-arm PEG-succinimidyl succinate ester, 4-arm PEG-glutaramide succinimidyl ester, 8-arm PEG-glutaramide succinimidyl ester, 4-arm PEG-succinimide succinimidyl ester, 8-arm PEG-succinimide succinimidyl ester, 4-arm PEGepoxide, 8-arm PEG-epoxide, 4-arm PEG 4-nitrophenyl carbonate (NPC), 8-arm PEG 4-nitrophenyl carbonate (NPC), 4-arm PEG-acetic acid, 8-arm PEG-acetic acid, 4-arm PEG-glutaric acid, 8-arm PEG-glutaric acid, 4-arm PEG-succinic acid, 8-arm PEG-succinic acid, 4-arm PEGglutaramide acid, 8-arm PEG-glutaramide acid, 4-arm PEG-succinimide acid, 8-arm PEGsuccinimide acid, 4-arm PEG-azide, 8-arm PEG-azide, 4-arm PEG-alkyne, or 8-arm PEG-alkyne.

15. The polymer composition of claim 1, wherein the polymer composition further comprises a covalently attached biomolecule comprising a protein, a transcription factor, a nucleic acid, a deoxyribonucleic acid, a ribonucleic acid, a polynucleotide, a double-stranded DNA (dsDNA), a single stranded DNA (ssDNA), a hybrid double-stranded polynucleotide comprising a ssDNA and a ssRNA, an oligonucleotide, a carbohydrate, a hormone, a glycoprotein, an immunoglobulins, an antibody, or antigen-binding antibody fragment.

16. The polymer composition of claim 15, wherein the covalently attached biomolecule comprises a double-stranded DNA (dsDNA) or a protein.

17. A biosurface comprising a polymer composition of claim 1 disposed as a layer on a sensor.

18. A biosurface comprising the polymer composition of claim 1, wherein the biosurface is prepared by crosslinking the polymers, wherein a crosslinking attachment is derived from a decomposition reaction of an azide ($-N_3$), a diazo ($-N_2$) group, an aryl azide, an acyl azide, an azidoformate, a sulfonyl azide, a phosphoryl azide, a diazoalkane, a diazoketone, a diazoacetate, a diazirine, an aliphatic azo, an aryl ketone, benzophenone, acetophenone, anthraquinone, or an anthrone.

19. The polymer composition of claim 1, wherein the PEG polymer is derivatized with an N-hydroxysuccinimide (NHS) ester and wherein the derivatized PEG polymer has a molecular weight of from about 200 Da to about 1000 Da.

20. The polymer composition of claim 1, wherein the PHEMA polymer has a molecular weight from about 16,000 Da to about 45,000 Da.

* * * * *